(12) United States Patent
Takenaka et al.

(10) Patent No.: US 10,309,876 B2
(45) Date of Patent: Jun. 4, 2019

(54) CARTRIDGE FOR AIRBORNE SUBSTANCE SENSING DEVICE, AND AIRBORNE SUBSTANCE SENSING DEVICE

(71) Applicant: Hitachi, Ltd., Chiyoda-ku, Tokyo (JP)

(72) Inventors: Kei Takenaka, Tokyo (JP); Shigenori Togashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 169 days.

(21) Appl. No.: 15/025,299

(22) PCT Filed: Oct. 3, 2013

(86) PCT No.: PCT/JP2013/076928
§ 371 (c)(1),
(2) Date: Mar. 28, 2016

(87) PCT Pub. No.: WO2015/049759
PCT Pub. Date: Apr. 9, 2015

(65) Prior Publication Data
US 2016/0223435 A1  Aug. 4, 2016

(51) Int. Cl.
*G01N 1/22* (2006.01)
*C12Q 1/24* (2006.01)
(Continued)

(52) U.S. Cl.
CPC .............. *G01N 1/2247* (2013.01); *C12Q 1/24* (2013.01); *G01N 1/2205* (2013.01);
(Continued)

(58) Field of Classification Search
CPC ......... G01N 1/2208; G01N 2001/2244; G01N 1/2273; G01N 15/0625; G01N 15/0612
(Continued)

(56) References Cited

U.S. PATENT DOCUMENTS 5,425,802 A * 6/1995 Burton et al. ......... B01D 45/06
209/143
5,905,038 A * 5/1999 Parton .................. B01L 3/0275
422/419
(Continued)

FOREIGN PATENT DOCUMENTS

JP     2004-101354 A    4/2004
JP     2005-227051 A    8/2005
(Continued)

OTHER PUBLICATIONS

Machine translation of WO 2012114458 Al, Date: Aug. 30, 2012, Publisher: Google.com/patents, p. 9.*
(Continued)

*Primary Examiner* — Daniel S Larkin
(74) *Attorney, Agent, or Firm* — Crowell & Moring LLP

(57) ABSTRACT

An airborne substance sensing device is capable of blocking fluorescence that is not from an airborne substance and detecting faint fluorescence of an airborne substance with a high degree of accuracy through the use of a cartridge having an introduction plate in which micropores are formed through which a gas including an airborne substance can pass. A transparent collection plate opposes the introduction plate, and the airborne substance can be made to collide on the plate and be collected through the collision of the gas having passed through the micropores. In a main body, the introduction and collection plates are disposed in parallel, and a flow path for guiding the gas including the airborne substance to the micropores is formed. An opaque mask covers the collection plate and is provided with an opening window through which light can pass at a position corresponding to a collection area.

18 Claims, 20 Drawing Sheets

(51) Int. Cl.
| | | |
|---|---|---|
| *G01N 15/06* | (2006.01) | |
| *G01N 15/14* | (2006.01) | |
| *G01N 21/64* | (2006.01) | |
| *G01N 33/497* | (2006.01) | |
| *G01N 33/483* | (2006.01) | |
| *G01N 15/00* | (2006.01) | |
| *G01N 35/00* | (2006.01) | |
| *G01N 15/10* | (2006.01) | |

(52) U.S. Cl.
CPC ......... *G01N 1/2208* (2013.01); *G01N 1/2273* (2013.01); *G01N 15/0612* (2013.01); *G01N 15/0625* (2013.01); *G01N 15/1463* (2013.01); *G01N 21/6428* (2013.01); *G01N 33/4833* (2013.01); *G01N 33/497* (2013.01); *G01N 35/00069* (2013.01); *G01N 2001/227* (2013.01); *G01N 2001/2223* (2013.01); *G01N 2001/2244* (2013.01); *G01N 2015/0046* (2013.01); *G01N 2015/1006* (2013.01); *G01N 2015/1465* (2013.01); *G01N 2015/1497* (2013.01); *G01N 2021/6439* (2013.01); *G01N 2033/4975* (2013.01)

(58) Field of Classification Search
USPC ........... 73/23.3, 28.05, 863.22; 436/900, 181
See application file for complete search history.

(56) References Cited

U.S. PATENT DOCUMENTS

| | | |
|---|---|---|
| 2005/0153356 A1 | 7/2005 | Okawa et al. |
| 2006/0234209 A1 | 10/2006 | Walker et al. |
| 2011/0171684 A1* | 7/2011 | Yamamoto ............... C12Q 1/04 435/39 |
| 2011/0183371 A1* | 7/2011 | Noda et al. ............ C12Q 1/008 435/39 |
| 2013/0099143 A1 | 4/2013 | Mogami et al. |
| 2013/0319239 A1 | 12/2013 | Takenaka et al. |
| 2015/0010902 A1 | 1/2015 | Takenaka et al. |
| 2015/0377762 A1 | 12/2015 | Takenaka et al. |

FOREIGN PATENT DOCUMENTS

| | | |
|---|---|---|
| JP | 2005-274355 A | 10/2005 |
| JP | 2005-533502 A | 11/2005 |
| JP | 2006-300797 A | 11/2006 |
| JP | 2009-156715 A | 7/2009 |
| JP | 2012-13550 A | 1/2012 |
| WO | WO 2012/114458 A1 | 8/2012 |
| WO | WO 2013/118259 A1 | 8/2013 |
| WO | WO 2014/118898 A1 | 8/2014 |

OTHER PUBLICATIONS

Japanese-language Office Action issued in counterpart Japanese Application No. 2015-540318 dated Sep. 13, 2016 with partial English translation (Eight (8) pages).

International Search Report (PCT/ISA/210) issued in PCT Application No. PCT/JP2013/076928 dated Jan. 7, 2014 with English translation (Four (4) pages).

Takenaka, K., et al., "Kokichu Biseibutsu no Jinsoku Kenchi System no Kaihatsu", The Society of Chemical Engineers, $78^{th}$ Annual Meeting, Osaka, Japan, Feb. 17, 2013, p. J122 with partial English translation (Four (4) pages).

Takenaka, K., et al., "Micro Kagaku Process o Riyo shita Mist Hyoshikiho ni yoru Kukichu Virus Kenchi no Tanjikanka", The Society of Chemical Engineers, 44th Annual Meeting, Sendai, Japan, Aug. 19, 2012, p. I302 with partial English translation (Five (5) pages).

Takenaka, K., et al., "Micro Kagaku Process o Mochiita Mist Hyoshikiho ni yoru Virus Jinsoku Kenchi," The Society of Chemical Engineers, 77th Annual Meeting, Tokyo, Japan, Feb. 2012, E114, p. 169, with partial English translation of description of Figure 3 (four (4) pages).

\* cited by examiner

CARTRIDGE FOR AIRBORNE SUBSTANCE SENSING DEVICE, AND AIRBORNE SUBSTANCE SENSING DEVICE

TECHNICAL FIELD

The present invention relates to a cartridge used for an airborne substance sensing device for detecting an airborne substance such as microparticles contained in the air or breath, and an airborne substance sensing device using this cartridge.

BACKGROUND ART

It is very important to prevent spread of an infection such as influenza or tuberculosis for a safe and secure social life. It is considered that these infections spread by suction of a splash containing a microorganism such as bacteria or viruses released from a body of a patient into the atmosphere into a body of another person. A powerful means for preventing spread of the infections is to find and isolate an infected person early. Various diagnostic methods are used in a medical site.

For example, in diagnosis of a respiratory infection such as influenza, a simple kit for sensing an antigen of a microorganism such as viruses or bacteria contained in a body fluid using an immunochromatography method is often used. However, the diagnosis using the simple kit requires collecting a body fluid by inserting a swab into the nasal cavity of a patient, and may be rejected, for example, by a very young patient due to pain. In general, a simple kit has a low sensitivity, and cannot necessarily secure a sufficient amount of antigen of a microorganism in a patient in an early stage of infection. When the amount of antigen of a collected microorganism is small, negative determination will be made. The activity of inserting a swab into the nasal cavity of a patient is a medical activity; therefore, the activity is limited to medical workers.

Therefore, a method for sensing a microorganism more simply has been demanded. With respect to this demand, a method for directly collecting a microorganism such as viruses or bacteria floating in the air from breath and sensing the microorganism optically has been proposed.

For example, PTL 1 describes a technique of a method for capturing a microorganism by a membrane method and sensing the microorganism. Specifically, a membrane (filter) having pores is disposed between two members of an upper surface part and a bottom part, and a microorganism included in a fluid and having a size larger than the pore is captured by this membrane. Thereafter, the captured microorganism is stained with a visualization reagent, and is imaged by a CCD camera for image processing, or is observed and analyzed using an electron microscope or the like.

In the method for directly collecting a microorganism in the air using such a membrane as described in PTL 1, a microorganism can be collected without giving pain to a patient, and the method is not a medical activity. Therefore, the method can be performed also by a person other than a medical worker. In addition, bacteria collected on the membrane is sensed directly. Therefore, collecting and sensing can be performed automatically and continuously.

PTL 2 describes a technique of an analyzer in which a target component is bonded to a spot on a chip by an antigen-antibody reaction or nucleic acid hybridization, a fluorescence dye is then bonded to the target component, and the fluorescence amount derived from the target component is measured with an optical system device. This analyzer includes a gap disposed for each spot on a stand for holding the chip in order to optically separate fluorescence derived from the target spot and fluorescence derived from an adjacent spot from each other. The gap functions as an optical mask.

In such a method for measuring the fluorescence amount of a measurement object such as DNA as described in PTL 2, it is possible to determine presence of the measurement object more rapidly than in image analysis. The measurement object can be sensed with high sensitivity by disposing a mask transmitting fluorescence derived from the measurement object and blocking fluorescence derived from a substance other than the measurement object.

CITATION LIST

Patent Literatures

PTL 1: 2005-533502 W
PTL 2: 2005-227051 A

SUMMARY OF INVENTION

Technical Problem

In the method described in PTL 1, it is necessary to acquire an image enlarged at a high magnification in order to determine the shape of bacteria having a size of several μm, and a long period of time is needed for acquiring an image of an entire membrane surface having several mm$^2$ and determining a microorganism. As a result, it is difficult to acquire an examination result rapidly.

In the method described in PTL 1, a position on the filter, on which a microorganism is collected, cannot be predicted. Therefore, it is difficult to select only fluorescence of the microorganism by masking a position where the microorganism as a measurement object has not been collected using the method described in PTL 2. Therefore, in this method, it is considered that it is difficult to sense a microorganism in a small amount with high sensitivity.

The present invention has been achieved in view of the above problems in prior art. An object thereof is to provide an airborne substance sensing device for sensing a substance in the air or breath simply and rapidly, and a cartridge used therefor.

Solution to Problem

In order to solve the above problems, a cartridge for an airborne substance sensing device of the present invention includes an introduction plate on which a micropore through which a gas containing an airborne substance can pass is formed, a transparent collection plate disposed so as to face the introduction plate and capable of collecting an airborne substance by collision of the airborne substance due to collision of a gas which has passed through the micropore, a main body in which the introduction plate and the collection plate are disposed in parallel and a flow path for guiding the gas containing the airborne substance to the micropore is formed, and an opaque mask covering the collection plate and provided with an opening window through which light can pass at a position corresponding to a collection area on the collection plate in which the airborne substance is collected by collision.

The airborne substance sensing device according to the present invention uses the above cartridge for an airborne substance sensing device, and includes a pump for generating a flow of the air in a direction from the introduction plate to the collection plate, and an optical sensor for optically sensing an airborne substance captured on the collection plate. The optical sensor is disposed on the rear side of a collecting surface of the collection plate.

According to the present invention, the opaque mask covering the collection plate is provided with an opening window through which light can pass at a position corresponding to a collection area. Therefore, when an airborne substance collected on the collection plate is sensed fluorescently with the optical sensor, it is possible to prevent fluorescence emitted at a position other than the collection area of the collection plate from reaching the optical sensor, to consequently select only faint fluorescence generated by the airborne substance collected on the collection plate, and to sense the airborne substance with high sensitivity.

Advantageous Effects of Invention

The present invention exhibits such an extremely excellent effect that it is possible to sense an airborne substance such as a microorganism in breath with high sensitivity regardless of skill of an examiner by collecting and detecting the airborne substance rapidly and automatically, and to early find a patient with an infection simply, rapidly, and with high sensitivity.

DESCRIPTION OF EMBODIMENTS

As described above, in order to prevent spread of an infection, it is important to find and isolate a patient early. For this, it is required to collect a microorganism in a body of a patient simply and to sense the microorganism simply, rapidly, and with high sensitivity. Therefore, the inventors of the present invention made intensive studies of a method and a device for sensing a microorganism in the air or breath rapidly. As a result, the inventors have reached the present invention.

Hereinafter, some preferable Examples according to the present invention will be described with reference to the drawings. In the present invention, "airborne substance" as a sensing object is a micro substance contained in a gas such as the air or breath. As an example, "microorganism contained in the air or breath" means a wider area than a microorganism defined generally, and examples thereof include viruses, bacteria, yeast, protozoa, fungi, spores, and pollen. In addition, examples of the airborne substance include animal skin debris, mite excrement and carcasses, house dust, and microparticles of exhaust gas particles and ore particles.

EXAMPLE 1

Figure 1:
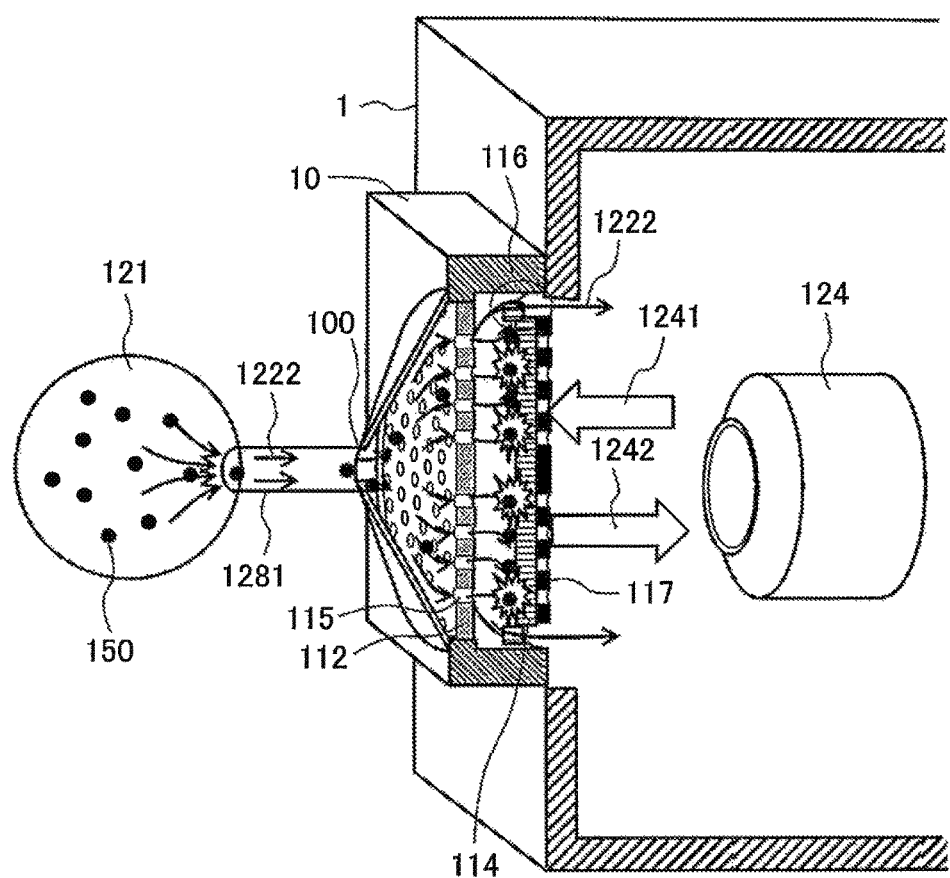
FIG. 1 is a schematic diagram illustrating a principle of a breath microorganism sensing device as an example of an airborne substance sensing device according to the present invention.

FIG. 1 is a schematic structural diagram illustrating a breath microorganism sensing device 1 as one type of the airborne substance sensing device according to the present invention. The breath microorganism sensing device 1 is illustrated by a partial cross sectional view. In the breath microorganism sensing device 1, a cartridge 10 is disposed so as to be detachable on one side surface of a main body of the sensing device formed in a box shape. A breath bag 121 in which breath of a patient collected at a place where the breath microorganism sensing device 1 is disposed or at a remote place is enclosed is coupled to the cartridge 10 through a coupling pipe 1281 described below. When microparticles such as exhaust gas particles are sensed, an air bag is used in place of the breath bag.

The cartridge 10 has a flat rectangular parallelepiped shape or a thick card shape, and holds a porous introduction plate 112 having a plurality of micropores 115 formed and a collection plate 114 disposed almost parallel to this introduction plate 112 with a small gap therebetween in a rectangular parallelepiped main body 110. An inlet port 100 is formed in the center of a flat side surface of the main body 110 in order to attach or detach the coupling pipe 1281 coupled to the breath bag 121.

In this way, the breath microorganism sensing device 1 includes the breath bag 121 in which breath of a patient is enclosed and the cartridge 10 coupled to the breath bag 121. The cartridge 10 includes the introduction plate 112 which is a plate having the plurality of micropores 115 formed and the transparent collection plate 114 for collecting a microorganism particle 150 which has passed through each of the micropores 115 on a surface thereof. The collection plate 114 is covered with an opaque mask 117 opened only in a collection area of the microorganism particle 150. In FIG. 1, there is a gap between a part of an end of the collection plate 114 and the cartridge 10, and this gap functions as a vent 116. By disposing the vent 116 for discharging the air or breath on an outer periphery, the center of the collection plate 114 can be irradiated with light easily, and the sensing sensitivity can be increased. The transparent collection plate 114 can prevent reflection or scattering of light, and generation of noise.

The opaque mask 117 covers the entire surface of the circular collection plate 114, and is provided with a transparent opening window 118 at a position corresponding to a collection area on the collection plate in which an airborne substance is collected by collision. The opening window 118 of the mask is disposed so as to overlap with the area in which an airborne substance is captured and so as to have an area the same as or larger than the area in which the airborne substance is captured. The number of the opening window 118 of the mask 117 is equal to that of the micropores 115 of the introduction plate 112. The opening window 118 of the mask 117 is aligned with each of the micropores 115 of the introduction plate 113 using an alignment mark or the like.

The breath microorganism sensing device 1 includes a pump (not illustrated in FIG. 1) described below in order to suck breath in the breath bag 121. The breath in the breath bag 121 is sucked to a side of the cartridge 10 in a direction of an arrow 1222 by the pump. The breath containing the microorganism particle 150 passes through the plurality of micropores 115, and then flows in a different direction around a surface of the collection plate 114. The breath flows outside the cartridge 10 from the vent 116 disposed on an outer periphery. The microorganism particle 150 in the breath deviates from an airstream due to an inertial force, and collide with the surface of the collection plate 114 to be collected. This method is generally referred to as an impaction method. Microorganism particles such as viruses are hardly removed when colliding with the collection plate 114 such as a glass plate, and therefore can be easily collected.

The breath microorganism sensing device 1 further includes an optical sensor 124 for optically sensing the microorganism particle 150 collected on the collection plate 114 of the cartridge 10 from the rear side of the collection plate 114. By sensing fluorescence 1242 of the microorganism particle 150 emitted when the microorganism particle 150 collected on the surface of the collection plate 114 is irradiated with excitation light 1241 from the optical sensor 124 with the optical sensor 124, the microorganism particle 150 in breath is sensed.

Detailed description will be given below with reference to FIGS. 4 and 5. By covering a part of the collection plate 114 other than the part where the microorganism particle 150 is collected (hereinafter, referred to as collection area), the mask 117 prevents fluorescence generated from a part other than the collection area from reaching the optical sensor 124. As a result, only faint fluorescence generated by the microorganism particle 150 on the collection plate 114 can be selected, and the microorganism particle 150 can be sensed with high sensitivity. Examples of the fluorescence generated from a part other than the collection area include fluorescence of the collection plate (autofluorescence).

Only by coupling the breath bag 121 into which a patient has blown breath to the cartridge 10 of the breath microorganism sensing device 1, an examiner can collect the microorganism particle 150 in breath on the surface of the collection plate 114 of the cartridge 10 automatically, and can automatically sense the microorganism particle 150 by fluorescence sensing with high sensitivity. Here, only the transparent collection plate 114 is disposed between the optical sensor 124 and the microorganism particle 150. Therefore, an influence by refraction, reflection, or scattering of light can be removed as much as possible. A part of the collection plate 114 other than the opening window 118 is covered with the opaque mask 117. Therefore, it is possible to detect even faint fluorescence generated by the microorganism particle 150.

Figure 2:
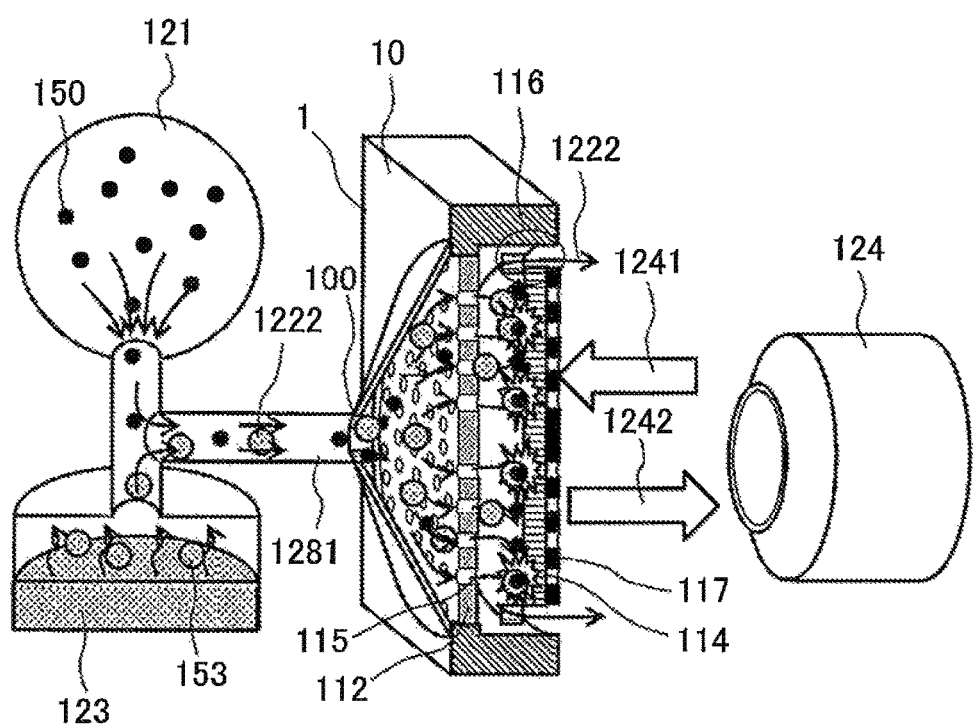
FIG. 2 is a schematic diagram illustrating a structure obtained by adding a fluorescence dye atomizing unit to the breath microorganism sensing device illustrated in FIG. 1.
Figure 3:
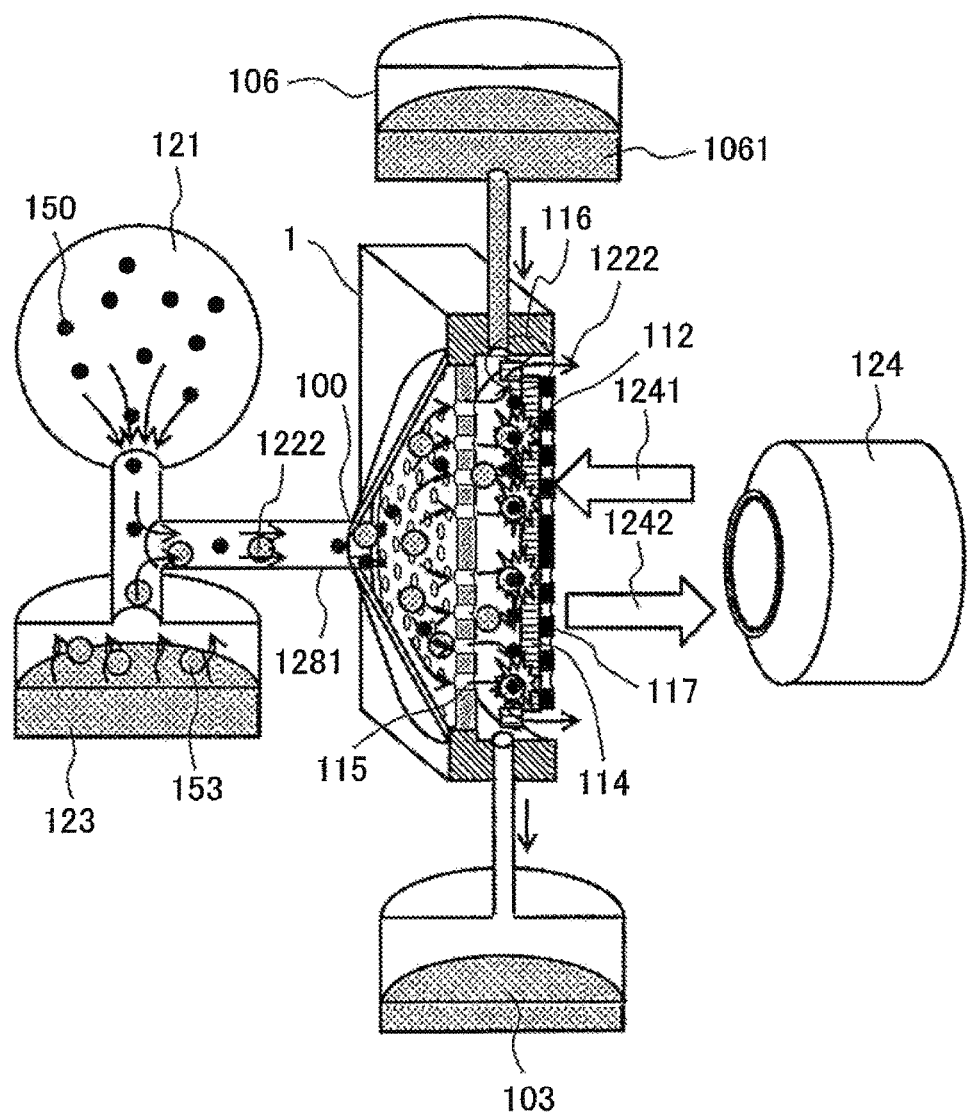
FIG. 3 is a schematic diagram illustrating a structure obtained by adding a reagent supply recover unit to the breath microorganism sensing device illustrated in FIG. 1.

Each of FIGS. 2 and 3 is a diagram illustrating a schematic structure of the breath microorganism sensing device 1 obtained by adding a structure for labeling the collected microorganism particle 150 with a specific fluorescence dye. When specific microorganisms of influenza virus, tuberculosis, and the like are sensed, by using a fluorescence dye specifically bonded to these microorganisms, the sensing sensitivity or determination performance is increased remarkably. For example, a fluorescently labeled anti-influenza virus antibody is used for an influenza virus, and a fluorescently labeled anti-tubercle bacillus antibody is used for a tubercle bacillus.

In the breath microorganism sensing device 1 in FIG. 2, in addition to the breath bag 121, an atomizer 123 for atomizing a liquid held therein is coupled to the cartridge 10. The atomizer 123 generates a mist 153 containing a fluorescence dye by atomizing a fluorescence dye liquid. The microorganism particle 150 is collected on the collection plate 114. Thereafter, the mist 153 generated by the atomizer 123 passes through the plurality of micropores 115, and then collides with the surface of the collection plate 114. The fluorescence dye contained in the mist 153 which has collided is specifically bonded to the microorganism particle 150 collected on the surface of the collection plate 114. By sensing the fluorescence 1242 of the fluorescence dye generated by the microorganism particle 150 with the optical sensor 124, the microorganism particle 150 can be sensed with high sensitivity.

Because of the same reason as the description for FIG. 1, the mask 117 transmits only faint fluorescence generated by the microorganism particle 150 on the collection plate 114 and blocks fluorescence generated from a part other than the collection area. Therefore, the microorganism particle 150 can be sensed with high sensitivity. Examples of the fluorescence generated from a part other than the collection area include fluorescence of the collection plate (autofluorescence) and fluorescence of a fluorescence dye attached to the surface of the collection plate 114.

The breath microorganism sensing device 1 in FIG. 3 is coupled to a reagent container 106 for holding a reagent 1061 in the cartridge 10 and a waste container 103 for discarding the reagent 1061. The breath microorganism sensing device 1 supplies the reagent 1061 to the surface of the collection plate 114 from the reagent container 106, and discards the supplied reagent 1061 to the waste container 103. By making the reagent 1061 include a fluorescence dye liquid or a cleaning liquid, it is possible to label the fluorescence dye to the microorganism particle 150 or clean the surface of the collection plate 114 by flow of the reagent 1061.

Figure 4A:
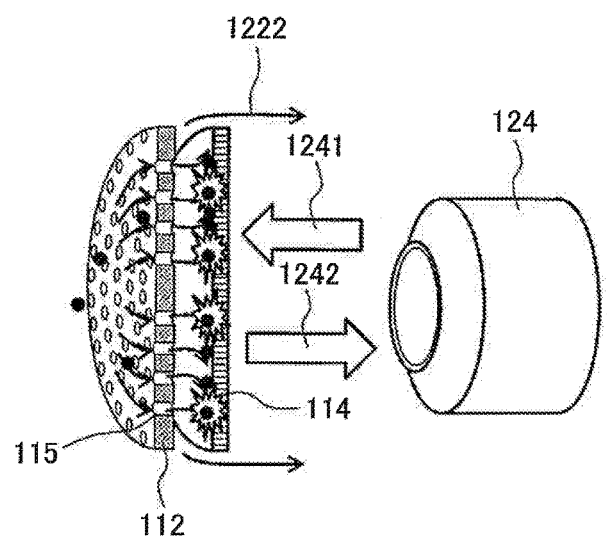
FIG. 4A is a diagram for describing a case where a microorganism is sensed by an optical sensor when a mask is not used in the breath microorganism sensing device.
Figure 4B:
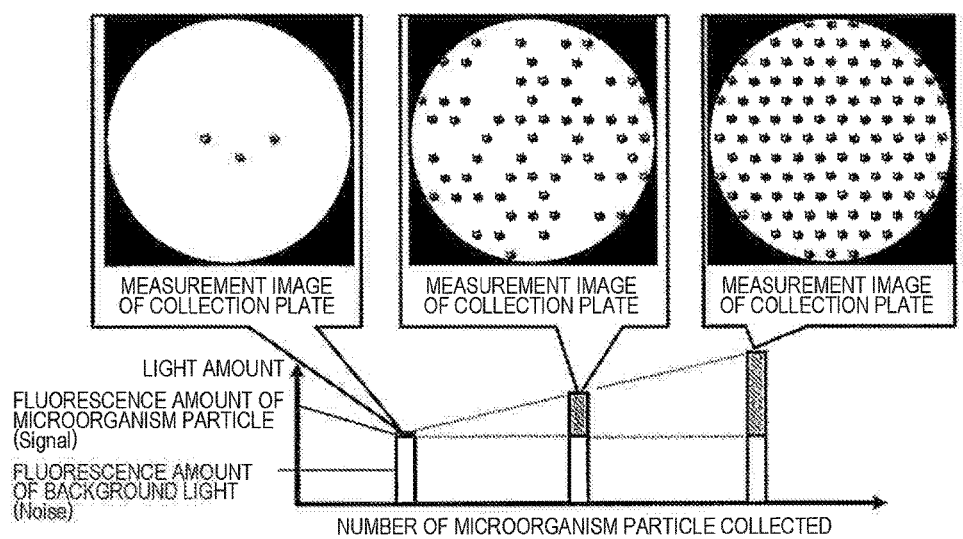
FIG. 4B is a diagram for describing a sensing state in FIG. 4A.

Next, an effect of the opaque mask 117 will be described with reference to FIGS. 4 and 5. FIG. 4A is a schematic structural diagram illustrating the breath microorganism sensing device obtained by cutting a part when a mask is not used. FIG. 4B illustrates a bar graph in which the horizontal axis indicates the number of the collected microorganism particle 150 and the vertical axis indicates the light amount of fluorescence incident on the optical sensor 124. The pictures accompanying the bar graph indicate fluorescence images of the microorganism particle 150 collected on the surface of the collection plate 114. The number of the collected microorganism particle 150 increases toward the right; therefore, the fluorescence amount also increases.

The fluorescence incident on the optical sensor 124 includes fluorescence generated by the collection plate (autofluorescence) and fluorescence generated by a substance such as a fluorescence dye attached to the surface of the collection plate in addition to fluorescence generated by the microorganism particle 150. The fluorescence generated by a substance other than the microorganism particle 150 is referred to as background light. When the number of the collected microorganism particle 150 is large, the fluorescence amount of the background light is negligible. However, when the number of the collected microorganism particle 150 is small, the fluorescence amount of the background light is not negligible. Therefore, in order to sense a small amount of the microorganism particle 150, it is necessary to reduce the amount of the background light incident on the optical sensor 124.

Figure 5A:
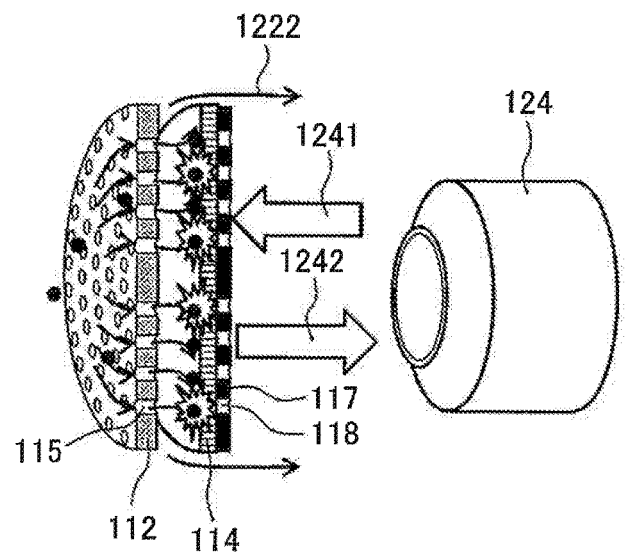
FIG. 5A is a diagram for describing a case where a microorganism is sensed by the optical sensor when a mask is used in the breath microorganism sensing device.
Figure 5B:
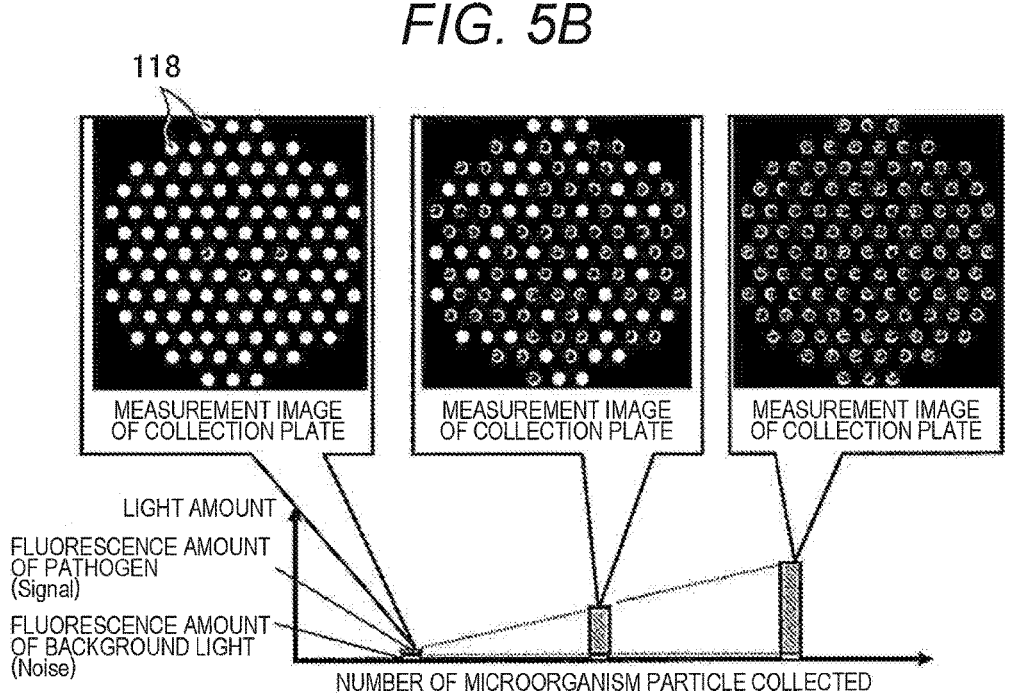
FIG. 5B is a diagram for describing a sensing state in FIG. 5A.

FIG. 5A is a schematic structural diagram illustrating the breath microorganism sensing device obtained by cutting a part when the mask 117 is used. In the impaction method, the area (collection area) on the collection plate 114 in which the microorganism 150 is collected by collision is the same as long as the size or the mass of the microorganism 150 collected, or the flow rate of the airstream passing through the micropores 115 is the same. Therefore, by examining the collection area by calculation or an experimental method and covering the collection plate 114 with the mask 117 provided with the opening window 118 at a position overlapping with the collection area, it is possible to prevent fluorescence from a substance other than the microorganism particle 150, generated from a part other than the collection area of the microorganism particle 150, from reaching the optical sensor 124. FIG. 5B illustrates a bar graph in which the horizontal axis indicates the number of the collected microorganism particle 150 and the vertical axis indicates the fluorescence amount in the optical sensor 124. Similarly to the above, the images accompanying the bar graph indicate images of the microorganism particle 150 collected on the surface of the collection plate 114. The number of the collected microorganism particle 150 increases toward the right.

A part other than the collection area of the microorganism particle 150 on the collection plate 114 is covered with the mask 117. Therefore, the background light generated from a part other than the collection area is blocked by the mask 117, and the amount of light incident on the optical sensor 124 is smaller than the amount in a case where a mask is not used (FIG. 4A). As a result, only faint fluorescence generated by the microorganism particle 150 on the collection plate 114 is selected; therefore, a small amount of the microorganism particles 115 can be sensed with high sensitivity.

Figure 6A:
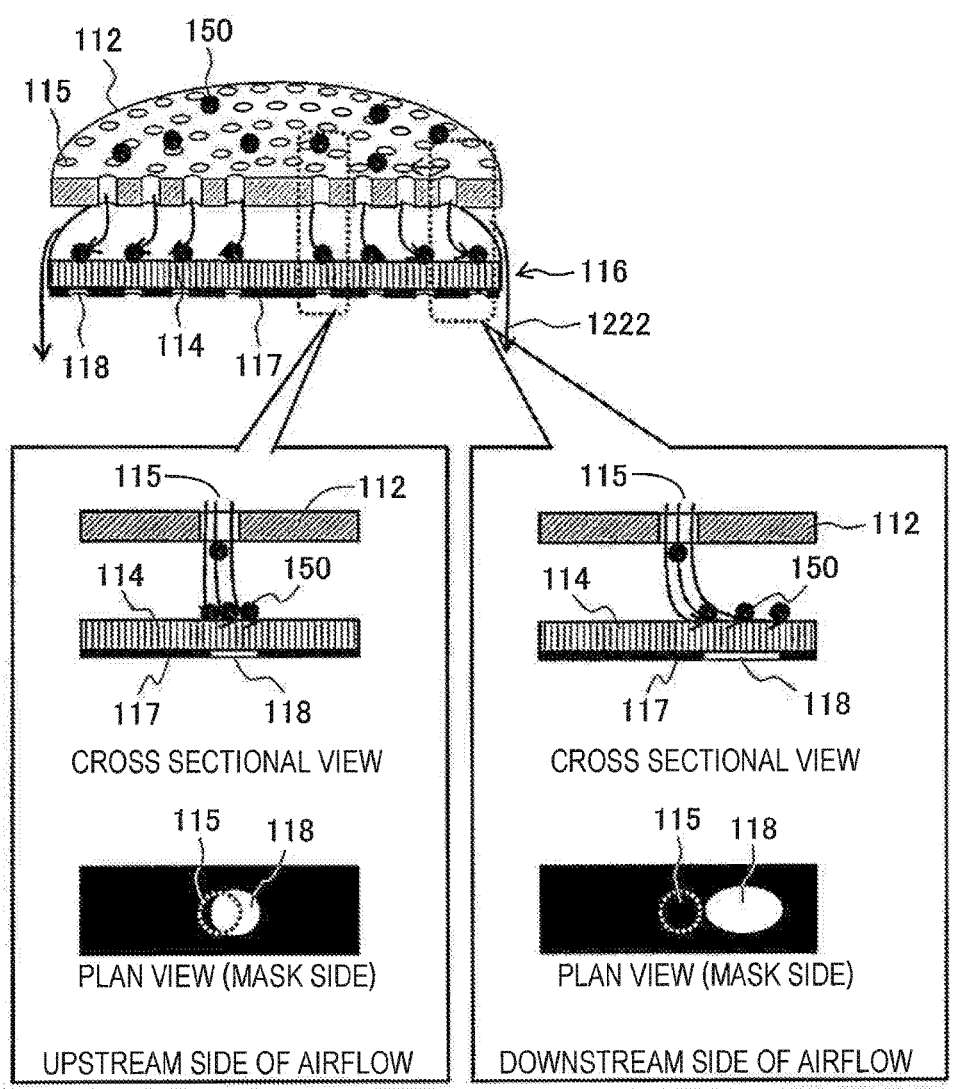
FIG. 6A illustrates a partially cutaway perspective view and a major cross sectional view for describing a position and a shape of an opening window disposed in an opaque mask.
Figure 6B:
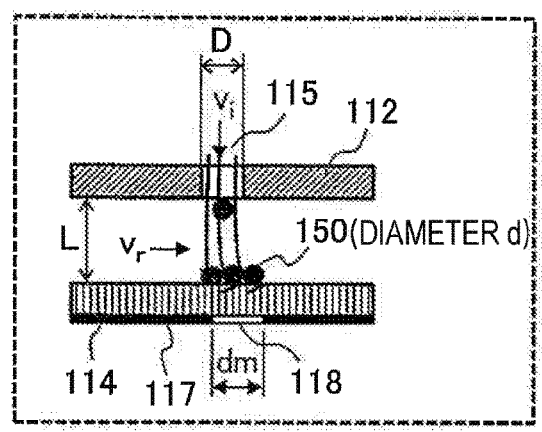
FIG. 6B is a major cross sectional view illustrating the opening window in FIG. 6A in detail.

FIGS. 6A and 6B are views for describing the position and the shape of the opening window 118 of the mask 117. Here, a case where the vent 116 is disposed on an outer periphery of the collection plate 114 is assumed. In this case, an airstream is generated on the collection plate 114 along the surface of the collection plate in a direction from the center to the outer periphery. Due to an influence by this airstream, the microorganism particles 150 which have passed through the micropores 115 positioned at further downstream of the airstream (outer periphery side of the introduction plate 112) collide with the collection plate 114 in an area deviating further from the positions of the micropores 115 in the airstream direction. The shape of the collision area is an oval-like shape extended in the airstream direction. Therefore, it is preferable to set the position of each opening window such that the opening window 118 positioned closer to the outer periphery of the collection plate 114 has a larger deviation amount. The opening window 118 preferably has a gradually larger deviation amount from the center toward the outer periphery.

The position and the shape of the collision area of the microorganism particle 150 depend on a parameter such as a diameter D of each of the micropores 115 through which the microorganism particle 150 passes, a gap L between the introduction plate 112 and the collection plate 114, a flow rate Vr of an airstream flowing between the introduction plate 112 and the collection plate 114, a flow rate Vi at which the airstream passes through the micropores 115, or a diameter d and a density ρ of the microorganism particle 150. Therefore, the position and the shape of the collision area are determined by calculation or an experimental method, and the position and the shape dm of the opening window 118 of the mask 117 are designed.

For example, when D is 70 μm, L is 300 μm, Vr is 15 m/sec, Vi is 100 m/sec, d is 0.3 μm, and ρ is 1.2 kg/m$^3$, 90% or more of the microorganism particles 150 which have passed through the micropores 115 can be collected. However, the center axis (gravity axis) of the collision area and the center axis of each of the micropores deviate downstream of the airstream (in a direction from the center of the collection plate to the outer periphery) approximately by 40 µm (about a radius of each of the micropores), and the area of the collision area becomes nearly three times that of the micropores. In this way, the distance between the center axis of the area in which the microorganism particle 150 is captured and the center axis of each of the micropores 115 is set to be shorter than the diameter of each of the micropores 115.

In the impaction method, as a deviation amount of each of the micropores 115 on the introduction plate 112 from the collection area of the microorganism particle 150 increases, the number of the microorganism particle 150 which is not collected without colliding with the collection plate 114 increases. As seen from calculation and experimental results, when the deviation amount of the center axis of each of the micropores 115 from the center axis of the collection area is larger than the diameter of each of the micropores 115, the number of the microorganism particle 150 not collected becomes so large not to be negligible. Therefore, it is preferable to design the position and the shape of each of the micropores 115 such that the deviation amount of the center axis of the collision area from the center axis of each of the micropores is not larger than the diameter of each of the micropores 115 and that the area of the collision area of the microorganism particle 150 is not larger than four times the area of the micropores 115.

In the present Example, a case where the vent is disposed on the outer periphery side of the collection plate 114 has been described. However, when the vent is disposed at the center of the collection plate 114, an airstream toward the center is generated on the collection plate 114. Therefore, the microorganism particles 150 which have passed through the micropores 115 positioned closer to the center of the introduction plate 112 collide with an area more deviating to the center from the positions of the micropores 115.

Figure 7A:
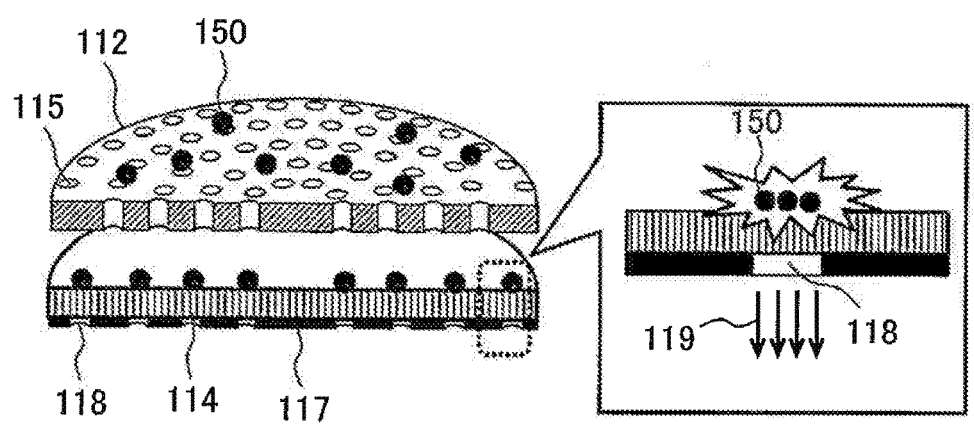
FIG. 7A is a major cross sectional view for describing a positional relation in a case where the opaque mask is disposed on an outer side of a collection plate.
Figure 7B:
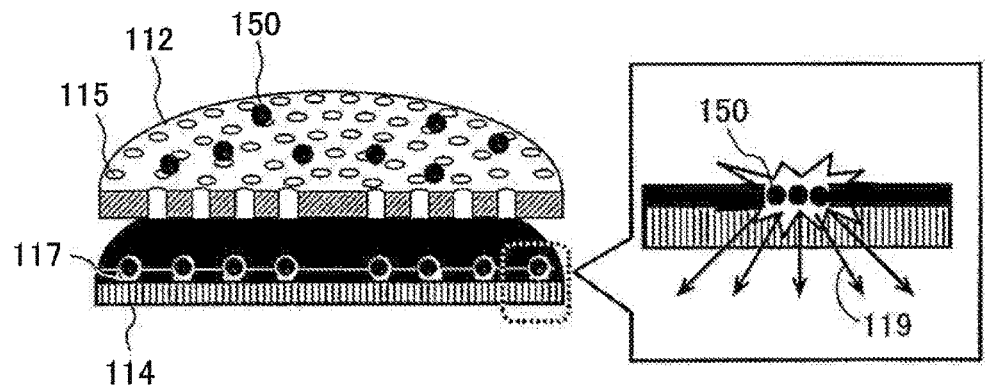
FIG. 7B is a major cross sectional view for describing a positional relation in a case where the opaque mask is disposed on an inner side of the collection plate.

FIGS. 7A and 7B are views for describing a positional relation between the opaque mask 117 and the collection plate 114. FIG. 7A illustrates a case where a surface of the mask 117 and a collection surface of the microorganism particle 150 are positioned on the face and rear surfaces of the collection plate 114, respectively. FIG. 7B illustrates a case where the surface of the mask 117 and the collection surface of the microorganism particle 150 are positioned on the same surface of the collection plate 114. In FIG. 7A, when the surface of the mask 117 and the collection surface are positioned on the face and rear surfaces, respectively, the collection surface of the microorganism particle 150 is apart from the surface of the mask 117 by the thickness of the collection plate 114. Therefore, a ratio (opening ratio) of fluorescence 119 passing through the opening window 118 with respect to the fluorescence 119 emitted by the microorganism particle 150 is smaller than the case where the surface of the mask 117 and the collection surface are positioned on the same surface in FIG. 7B. Therefore, in order to make a larger amount of fluorescence incident on the optical sensor 124, the surface of the mask 117 and the collection surface are preferably positioned on the same surface of the collection plate 114 (FIG. 7B).

Figure 8A:
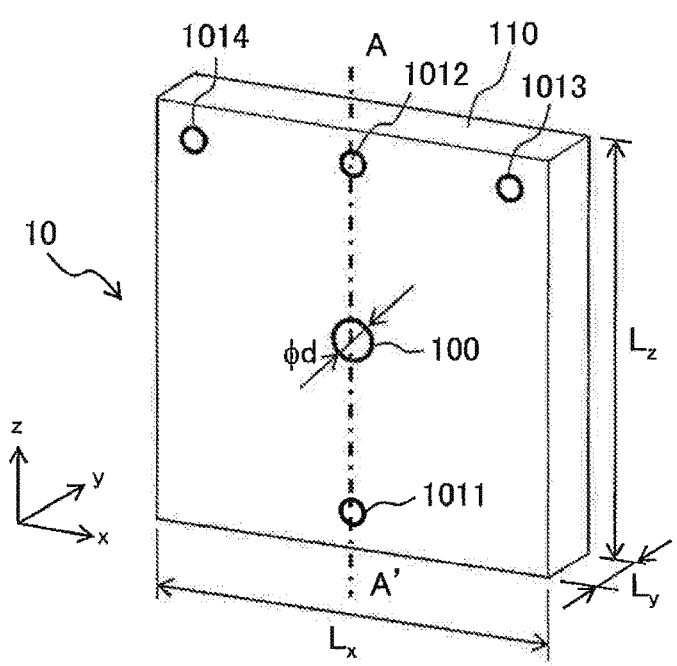
FIG. 8A is a perspective view of a cartridge in Example 1 of the present invention, viewed from a front side.
Figure 8B:
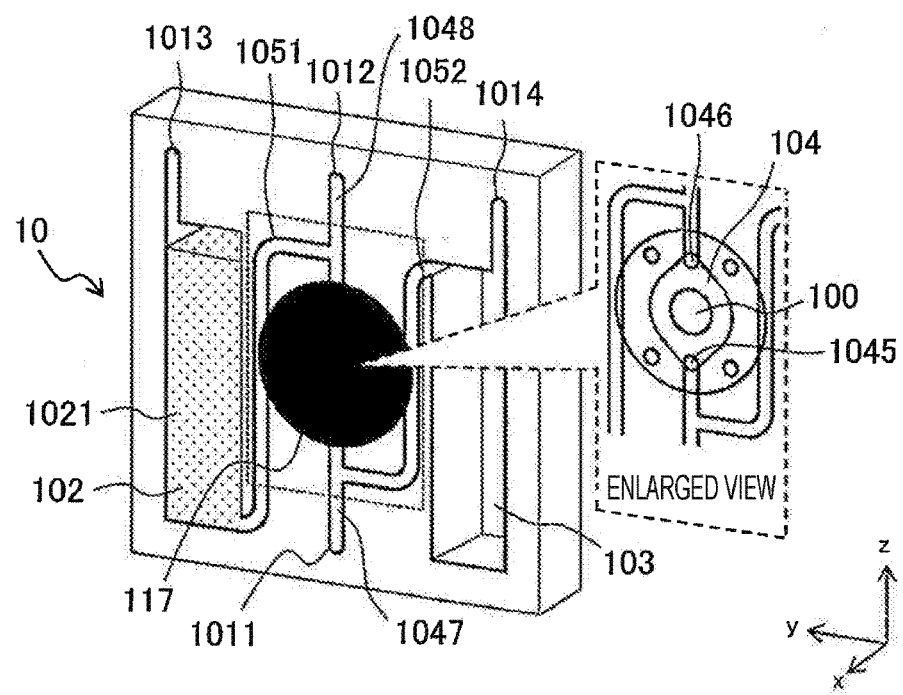
FIG. 8B is a perspective view of the cartridge in FIG. 8A, viewed from the rear side.
Figure 9A:
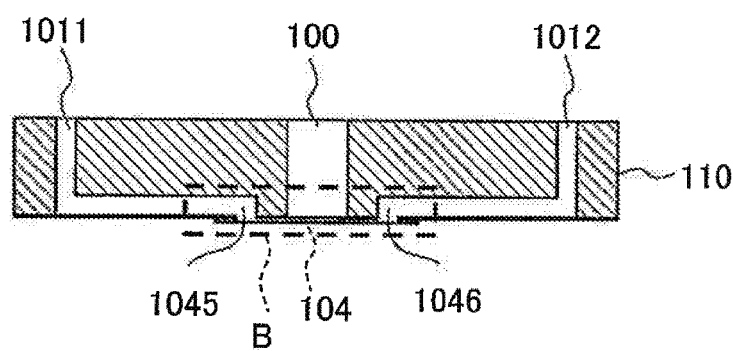
FIG. 9A is a cross sectional view cut along A-A line of the cartridge illustrated in FIG. 8A.
Figure 9B:
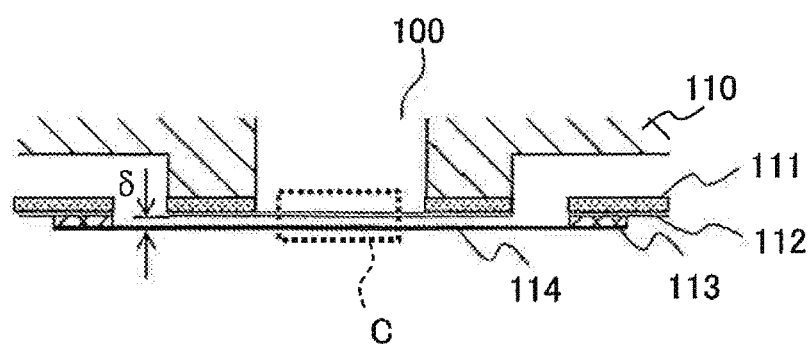
FIG. 9B is an enlarged view of a B portion of the cartridge illustrated in FIG. 9A.
Figure 9C:
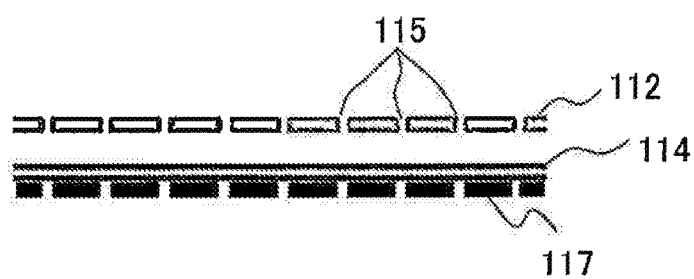
FIG. 9C is an enlarged view of a C portion of the cartridge illustrated in FIG. 9B.
Figure 10:
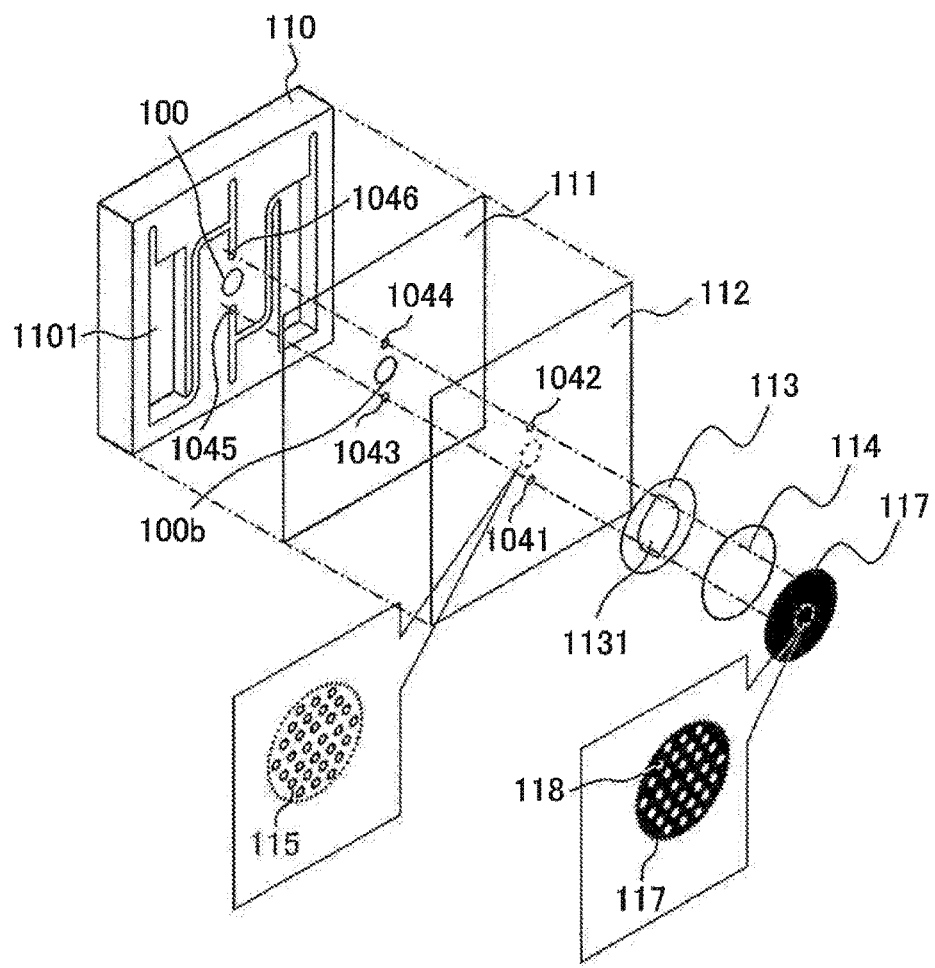
FIG. 10 is an exploded perspective view of the cartridge illustrated in FIGS. 8A and 8B.

Next, the cartridge 10 in the present invention will be described in detail with reference to FIGS. 8A to 10. FIG. 8A is a perspective view of the cartridge 10, viewed from a front side. FIG. 8B is a perspective view of the cartridge 10, viewed from the rear side. FIG. 9A is a cross sectional view cut along A-A' line in FIG. 8A. FIG. 9B is an enlarged view of a B portion in FIG. 9A. FIG. 9C is an enlarged view of a C portion in FIG. 9B. FIG. 10 is an exploded perspective view of the cartridge.

The cartridge 10 holds a liquid inside and has a structure for performing some steps necessary for collecting and sensing microorganisms in breath or the air. In the front central part of the main body 110 occupying the most part of the cartridge 10, the inlet port 100 to which the coupling pipe 1281 communicating with the breath bag 121 is coupled so as to be detachable is formed, and breath or the air containing microorganisms flows into the inlet port 100 from the breath bag 121. A plurality of vents 1011 to 1014 are formed on a periphery of the cartridge 10. A plurality of flow paths 1051, 1052, . . . are formed in the cartridge 10. Pressures in these flow paths are changed to be used for controlling flow of breath, a reagent, a cleaning liquid, or the like.

The cartridge 10 includes the inlet port 100 into which breath or the air containing microorganisms flows, the vents 1011 to 1014 for changing the atmosphere in the cartridge 10, a collecting and sensing part 104 for collecting and sensing microorganisms, a cleaning liquid container 102 for holding a cleaning liquid 1021 for cleaning the collecting and sensing part 104, the waste container 103 for discarding the cleaning liquid 1021 which has passed through the collecting and sensing part 104, a cleaning liquid container-collecting and sensing part coupling flow path 1051 for coupling the cleaning liquid container 102 to the collecting and sensing part 104 and making the cleaning liquid 1021 flow therein, and a collecting and sensing part-waste container coupling flow path 1052 for coupling the collecting and sensing part 104 to the waste container 103 and making the cleaning liquid 1021 flow therein.

The enlarged view in FIG. 8B is a view for understanding the position of the inlet port 100 or the collecting and sensing part 104 in the cartridge 10, and does not illustrate the mask 117. A vent path 1012 is coupled to the coupling flow path 1051 to form a coupling part 1046 to the collecting and sensing part 104. A vent path 1011 is coupled to the coupling flow path 1052 to form a coupling part 1045 to the collecting and sensing part 104. Here, a side of the cleaning liquid container 102 is defined as an upstream side and a side of the waste container 103 is defined as a downstream side along the flow of the cleaning liquid.

A branching flow path 1048 branching into two is formed at an end of the communicating flow path 1051 between the cleaning liquid container 102 and the collecting and sensing part 104. One has the vent 1012 at an end, and the other extends to the collecting and sensing part 104 to form the coupling part 1046 to the collecting and sensing part 104. Similarly, a branching flow path 1047 branching into two is formed at an end of the communicating flow path 1052 between the waste container 103 and the collecting and sensing part 104. One has the vent 1011 at an end, and the other extends to the collecting and sensing part 104 to form the coupling part 1045 to the collecting and sensing part 104.

The cartridge 10 is formed so as to have a length of 10 mm to 300 mm in an x direction and a z direction and a length of 3 mm to 100 mm in a y direction. The inlet port 100 is formed so as to have a diameter φd of 1 mm to 100 mm. The volume of the cleaning liquid container 102 is formed so as to hold 0.1 ml to 100 ml of the cleaning liquid 1021 inside. Each of the coupling flow path 1051 between the cleaning liquid container 102 and the collecting and sensing part 104 and the coupling flow path 1014 between the collecting and sensing part 104 and the waste container 103 is formed so as to have a depth or a flow path width of 0.1 mm to 10 mm. Typically, Lx and Lz are about 60 mm, and Ly is about 10 mm.

A cross sectional view of the cartridge 10 is illustrated in FIGS. 9A to 9C, and an exploded perspective view thereof is illustrated in FIG. 10. FIG. 9A is a cross sectional view cut along A-A' line in FIG. 8A. FIG. 9B is an enlarged cross sectional view of the collecting and sensing part 104 in the cartridge 10. FIG. 9C is an enlarged cross sectional view of an area 105 of the collecting and sensing part 104. Components of the cartridge 10, and preferable materials and sizes thereof will be described with reference to FIGS. 9 and 10.

The cartridge 10 includes the main body 110 provided with the inlet port 100, the introduction plate 112 provided with the one or more micropores 115, the collection plate 114 which is a transparent flat plate for collecting microorganisms on a surface thereof, the opaque mask 117 covering the collection plate 114, an adhesive layer 111 for bonding the main body 110 to the introduction plate 112, and a spacer 113 which is a ring-shaped component for bonding the introduction plate 112 to the collection plate 114 and disposing a space between the two components. By bonding these components to one another, a container or a flow path is formed in the cartridge 10.

As described above, the containers 102 and 103, the flow paths 1047, 1048, 1051, and 1052, and vents 1011 to 1014, 1045, and 1046 are formed in the main body 110. A water-resistant resin material is used for the main body 110 considering processability and manufacturing cost in order to form the containers 102 and 103, the flow paths 1047, 1048, 1051, and 1052, and the like easily. Examples of the water-resistant resin material include polypropylene, polyethylene terephthalate, polycarbonate, polystyrene, an acrylonitrile-butadiene-styrene resin, and polymethyl methacrylate. The containers 102 and 103, and the flow paths 1047, 1048, 1051, and 1052 are formed in the main body 110 using these materials by injection molding.

In the center of the adhesive layer 111, a communicating hole 100b is formed at a position corresponding to the inlet port 100 in the center of the main body 110, and communicating holes 1043 and 1044 are formed at positions corresponding to the coupling parts 1045 and 1046, respectively. In the center of the introduction plate 112, the plurality of micropores 115 are formed, and communicating holes 1041 and 1042 are formed at positions corresponding to the communicating holes 1043 and 1044 of the adhesive layer 111, respectively.

The ring-shaped spacer 113 having an opening 1131 formed in the center is bonded to a periphery of a part where the micropores 115 are formed on the rear side of the introduction plate 112. The spacer 113 has a shape of a sheet having an adhesive applied on both surfaces thereof. The collection plate 114 having almost the same outer diameter as the spacer 113 is bonded to a surface of the spacer 113 with an adhesive. The spacer 113 is interposed between the introduction plate 112 and the collection plate 114 to form a predetermined gap δ between these two kinds of plates 112 and 114 (refer to FIG. 9B). The opening window 118 of the opaque mask 117 covering the collection plate 114 is positioned corresponding to the opening 1131 of the spacer 112.

A transparent resin material such as polyethylene terephthalate, polymethyl methacrylate, or a cycloolefin polymer, which hardly generates stray light or autofluorescence, is preferably used for a material of the introduction plate 112 in order to reduce an influence to fluorescence sensing of microorganisms. The micropores 115 of the introduction plate 112 are formed by a micromachining method such as mechanical processing, ultrasonic processing, etching, or laser processing. In the impaction method, as the particle diameter of a microorganism collected is smaller, it is necessary to make the diameter of a micropore smaller, and as the suction amount is larger, it is necessary to make the number of the micropore larger. Therefore, an optimum diameter of each of the micropores 115 or the number of the micropore changes according to a measurement object.

For example, when an examination is performed using a virus particle having a diameter of 0.3 μm to 10 μm pollen having a diameter of several tens μm as a sensing object at a suction amount of 0.001 $m^3$/min to 1 $m^3$/min, the diameter of each of the micropores 115 is preferably from 0.01 m to 3 mm, the gap between the micropores 115 is preferably from 0.05 mm to 15 mm, and the number of the micropores 115 is preferably from 1 to 10,000. As an example, when breath containing a virus particle having a diameter of 0.3 μm or more is sucked at a suction amount of 0.003 $m^3$/min, the diameter of each of the micropores 115 is preferably 0.1 mm, the gap between the micropores 115 is preferably 0.6 mm, and the number of the micropores 115 is preferably 100.

The adhesive layer 111 is a component for bonding the main body 110 to the introduction plate 112. An acrylic or silicone adhesive is used therefor, or the adhesive layer 111 does not need to be used when bonding is performed by a method such as ultrasonic welding.

The spacer 113 is preferably formed of a water-resistant resin material in which both surface are adhesive. Examples thereof include resins such as polypropylene, polyethylene terephthalate, polycarbonate, polystyrene, an acrylonitrile-butadiene-styrene resin, and polymethyl methacrylate. In the impaction method, the thickness of the spacer 113 is preferably from one time to ten times the diameter of each of the micropores 115. For example, when the diameter of each of the micropores 115 is 0.1 mm, the thickness of the spacer 113 is preferably from 0.1 mm to 1 mm.

The collection plate 114 functions not only as a plate for collecting the microorganism particle 150 (FIG. 1) but also as an optical window when fluorescence sensing is performed with the optical sensor 124 (FIG. 1). The collection plate 114 also functions as a light-guiding path of the excitation light 1241 and the fluorescence 1242; therefore, the collection plate 114 needs to be formed of a material having an excellent optical characteristic. Therefore, it is preferable to use a material having a transmittance of 80% or more and small autofluorescence in a partial wavelength region in a near-ultraviolet to near-infrared wavelength region (300 nm to 800 nm). Preferable examples thereof include transparent resins such as glass, quartz, polyethylene terephthalate, polymethyl methacrylate, a cycloolefin polymer, and polydimethyl siloxane. A component obtained by bonding these members to one another may be used. The thickness of the collection plate 114 is preferably from 0.1 mm to 10 mm.

In order to surely collect the microorganism particle 150 which has collided, an adhesive material may be applied or stuck to the surface of the collection plate 114. Alternatively, the surface of the collection plate 114 may be modified with a material such as an antibody or an artificial antibody to be specifically bonded to a specific microorganism particle by physical bonding or chemical bonding.

The mask 117 requires a function to prevent fluorescence from a substance other than the microorganism particle 150 or reflected light of the excitation light 1241 from being incident on the optical sensor 124. Therefore, a material having a transmittance or a reflectivity of approximately zero and hardly generating autofluorescence is preferably used for the mask 117. Preferable examples thereof include an opaque resin material such as black polyethylene terephthalate or black polymethyl methacrylate, black anodized aluminum, and a resin plate or a metal plate having a black coating material applied thereon.

The opening window 118 of the mask 117 is formed by a micromachining method such as mechanical processing, ultrasonic processing, etching, or laser processing. As described above, the size and the position of the opening window 118 depend on the size and the position of each of the micropores 115 on the introduction plate 112. As illustrated in FIG. 6A, the position and the size of the opening window 118 positioned upstream of the airstream are almost the same as those of each of the micropores 115 facing the opening window 118. However, the size of the opening window 118 positioned downstream of the airstream is at most four times that of each of the micropores 115 facing the opening window 118, and the position thereof deviates downstream of the airstream.

Figure 11:
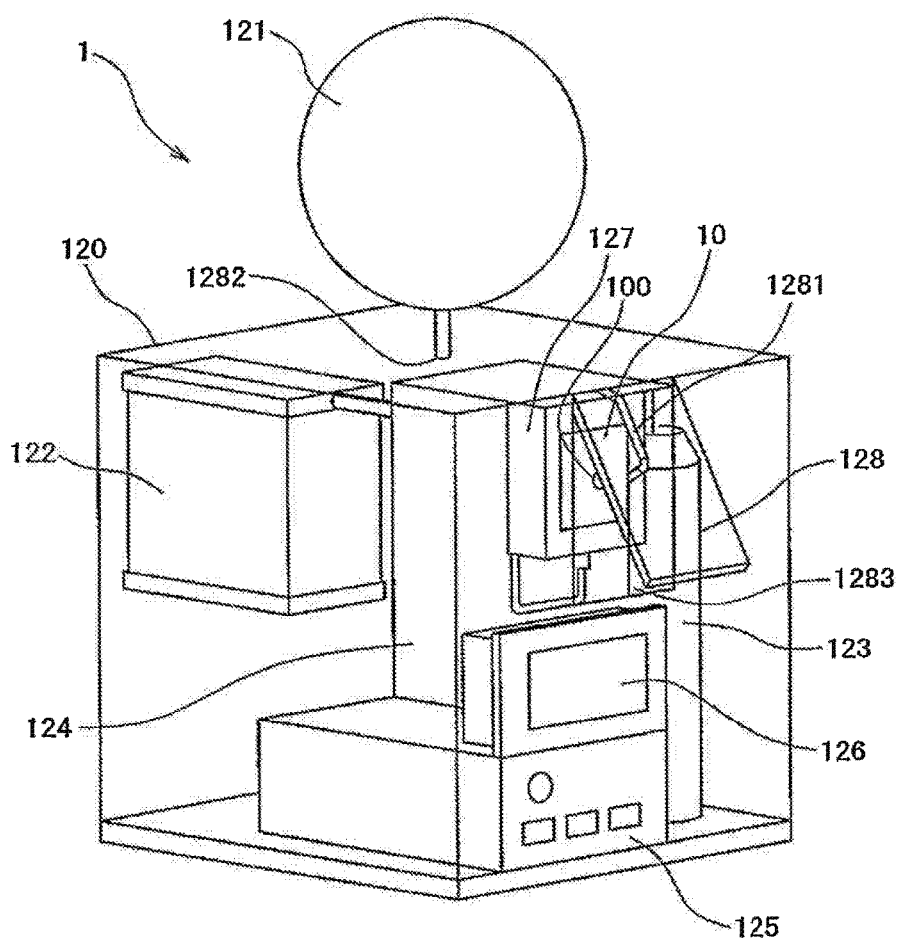
FIG. 11 is a perspective view illustrating an appearance of a breath microorganism sensing device using the cartridge illustrated in FIGS. 8A and 8B.

Next, the structure and a use method of the breath microorganism sensing device 1 will be described with reference to FIG. 11. FIG. 11 is a perspective view illustrating an appearance of the breath microorganism sensing device 1 using the cartridge 10. The breath microorganism sensing device 1 includes the breath bag 121 into which a patient has blown breath, the cartridge 10 for collecting and sensing microorganisms in breath, a cartridge holder 127 for holding the cartridge 10, an atomizer 128 for atomizing a liquid containing a fluorescence dye to be specifically bonded to microorganisms in breath, a pump 122 for sucking breath in the breath bag 121 or a mist of the fluorescence dye atomized by the atomizer 128 into the cartridge 10, and the optical sensor 124 for fluorescently sensing microorganism particles collected in the cartridge 10. The breath microorganism sensing device 1 includes a pipe for coupling the breath bag 121, the cartridge 10, the atomizer 128, and the pump 122 to one another, and a valve for opening or closing the pipe (not illustrated).

An attachment port 1282 of the breath bag 121 is fixed to the upper surface of the breath microorganism sensing device 1 in order to make the breath bag 121 detachable. The coupling pipe 1281 disposed so as to creep in the breath microorganism sensing device 1 is coupled to this attachment port 1282. An end of the coupling pipe 1281 can be fitted into a breath inlet 100 formed in the center of the cartridge 10.

The cartridge 10 for collecting and sensing microorganisms in breath is housed in the cartridge holder 127 disposed near a window 1283 formed in an upper side surface of the breath microorganism sensing device 1. An openable lid 128 is attached to the window 1283 in order to seal the breath microorganism sensing device 1 after the cartridge 10 is housed in the cartridge holder 127. The coupling pipe 1281 is attached to the lid 128. Therefore, when the lid 128 closes the window 1283, an end of the coupling pipe 1281 bent into an L shape is fitted into the inlet port 100 of the cartridge 10 automatically.

The optical sensor 124 for fluorescently sensing microorganism particles collected in the cartridge 10 is disposed on the rear side of the breath microorganism sensing device 1. The pump 122 for sucking breath in the breath bag 121 or a mist of the fluorescence dye atomized by an atomizing machine 128 into the cartridge 10 by reducing pressures in the flow paths 1051, 1052, and the like formed in the cartridge 10, is disposed on the rear side of the optical sensor 124.

An atomizing machine 123 for atomizing a liquid containing a fluorescence dye to be specifically bonded to microorganisms in breath is disposed on a side of the cartridge holder 127 in the breath microorganism sensing device 1. A controller 125 for controlling an action of the breath microorganism sensing device 1 and a display 126 for displaying examination contents or examination results are disposed below the cartridge holder 127. In FIG. 11, the controller 125 and the display 126 are incorporated into the breath microorganism sensing device 1. However, a system apparatus connected outside, such as a personal computer, may be substituted therefor.

Figure 12:
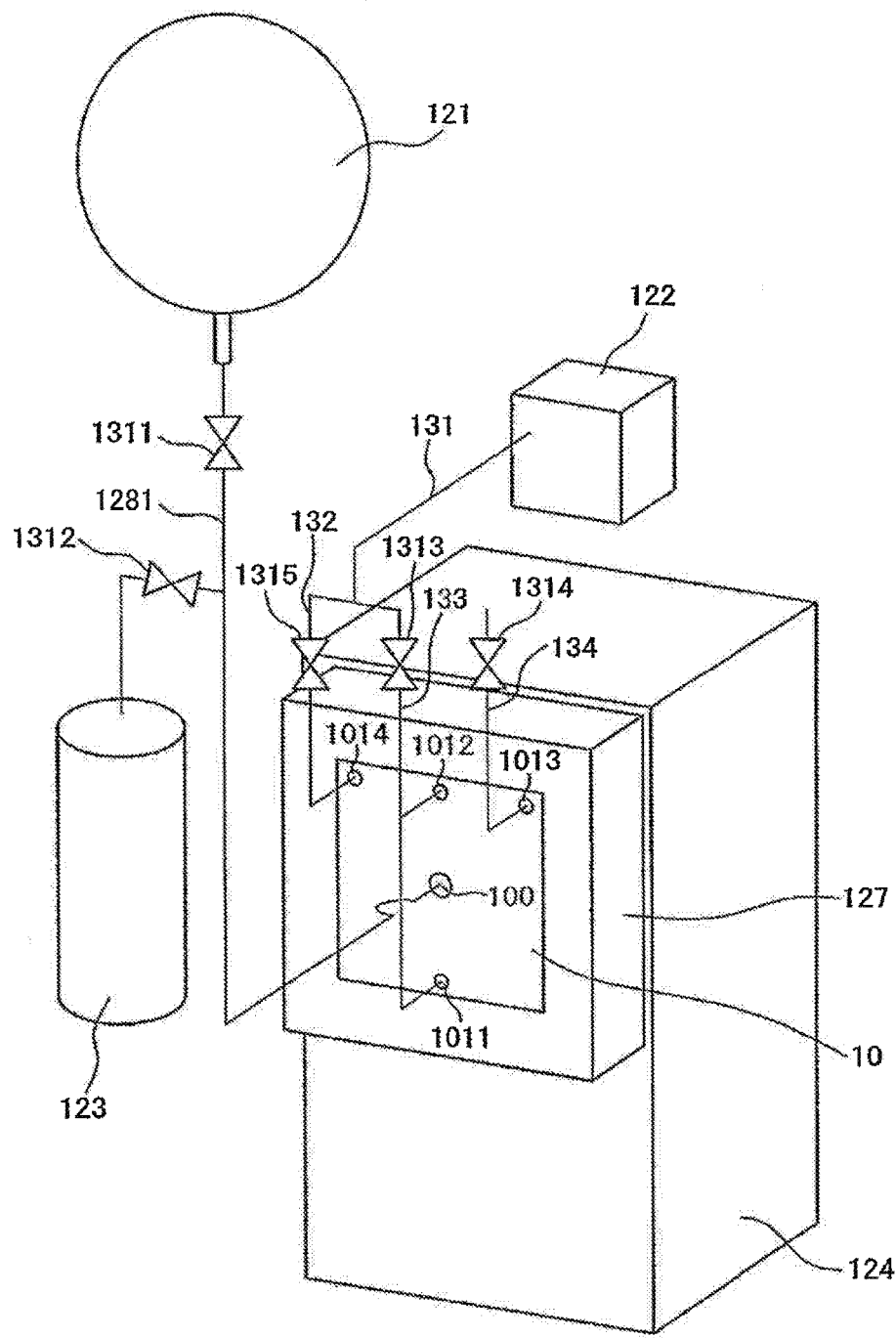
FIG. 12 is a diagram illustrating piping of the breath microorganism sensing device illustrated in FIG. 11.

FIG. 12 is a diagram illustrating a positional relation between a pipe 131 for coupling the breath bag 121, the cartridge 10, the atomizer 123, and the pump 122 to one another, and valves 1311 to 1315 for opening or closing the pipe 131 in the breath microorganism sensing device 1. The pipe 131 is coupled to the vents 1011 to 1014 of the cartridge 10.

In FIG. 12, a valve (not illustrated) for preventing collected breath from leaking after the breath is collected is formed in the breath bag 121. When the breath bag 121 is attached to the breath microorganism sensing device 1, this valve is opened automatically.

In the breath microorganism sensing device 1, the valve 1311 is disposed in the coupling pipe 1281 of the breath bag 121, and the valve 1312 is disposed in the middle of a pipe for the atomizing machine 123 branching from this coupling pipe 1281. As described above, an end of the coupling pipe 1281 is coupled to the inlet port 100 of the cartridge 10.

On the other hand, the inlet pipe 131 of the pump 122 branches into a plurality of pipes. A pipe 132 as one of these branches is coupled to the vent 1014 coupled to the waste container 103 of the cartridge 10. A pipe 133 as another branch is coupled to a vent 1012 communicating with the cleaning liquid container 102 and an air port 1011 communicating with the waste container 103. The pipe 132 has a valve 1315 interposed therein. The pipe 133 has a valve 1313 interposed therein. A pipe 134 exposed to the atmosphere is coupled to the vent 1013 communicating with the cleaning liquid container 102 of the cartridge 10. A valve 1314 is attached to this pipe 134. The above valves are disposed in the breath microorganism sensing device 1.

An examiner mounts the breath bag 121 into which a patient has blown breath and the cartridge 10 in the breath microorganism sensing device 1, closes the lid 128, specifies examination contents through the controller 125, and performs an examination. Here, breath of a patient has been used for an examination object. However, by enclosing the air of a life environment to be measured into the breath bag 121, it is also possible to sense exhaust gas particles and ore particles such as asbestos in addition to microorganism particles in the air of the life environment and allergens such as animal skin debris, mite excrement and carcasses, and house dust.

Next, sensing microorganism in breath will be described in detail with reference to FIGS. 13 and 14A to 14C and Table 1. Microorganism particles in breath are sensed according to the flowchart in FIG. 13. Table 1 indicates opening or closing of each of the valves 1311 to 1315, and actions of the pump 122 and the optical sensor 124 in each step of collecting, labeling, cleaning, and sensing. FIGS. 14A to 14C illustrate a state of flow in the cartridge 10, and states of the microorganism particle 150 and the fluorescence dye 154 on the collection plate 114 in each step of collecting, labeling, and cleaning.

TABLE 1

| Step | Valve | | | | | Pump | Sensor |
|---|---|---|---|---|---|---|---|
| | 1311 | 1312 | 1313 | 1314 | 1315 | 122 | 124 |
| Collecting | Open | Close | Open | Close | Close | On | Off |
| Labeling | Close | Open | Open | Close | Close | On | Off |
| Cleaning | Close | Close | Close | Open | Open | On | Off |
| Sensing | Open | Open | Open | Open | Open | Off | On |

Hereinafter, each step will be described.

(1) Preparation Step

When work for sensing microorganisms in breath is started, an examiner mounts the breath bag 121 into which a patient has blown breath and the cartridge 10 in the breath microorganism sensing device 1, and closes the lid 128. Thereafter, the examiner specifies examination contents through an input unit disposed in the controller 125, and performs an examination. The information is displayed on the display 126. The controller 125 checks whether a necessary tool, the cartridge 10, or the breath bag 121 is mounted in the breath microorganism sensing device 1 in step S310. When a necessary tool is not disposed or mounted, warning is displayed on the display 126 (step S300). When preparation is completed, a collecting step is started (S320). Hereinafter, each step of collecting, labeling, cleaning, and detecting will be described with reference to Table 1 and FIGS. 13 and 14A to 14C.

(2) Collecting Step

As illustrated in FIG. 14A, due to the open states (FIG. 12) of the valve 1311 of a pipe coupling the breath bag 121 to the inlet port 100 of the cartridge 10 and the valve 1313 coupling the vents 1011 and 1012 of the cartridge 10 to the pump 122, breath in the breath bag 121 flows in the inlet port 100 of the cartridge 10 and the vents 1011 and 1012 thereof by a suctioning action of the pump 122. Due to closed states of the valves 1314 and 1315 of a pipe coupled to the vents 1013 and 1014, the cleaning liquid 1021 in the cleaning liquid container 102 of the cartridge 10 stays in the container.

At this time, the microorganism particles 150 contained in breath pass through the micropores 115 on the introduction plate 112, and collide with the collection plate 114. The microorganism particle 150 which has collided is specifically bonded to an antibody 151 bonded to the surface of the collection plate 114; therefore, the microorganism particle 150 is collected on the surface of the collection plate 114.

(3) Labeling Step

Figure 13:
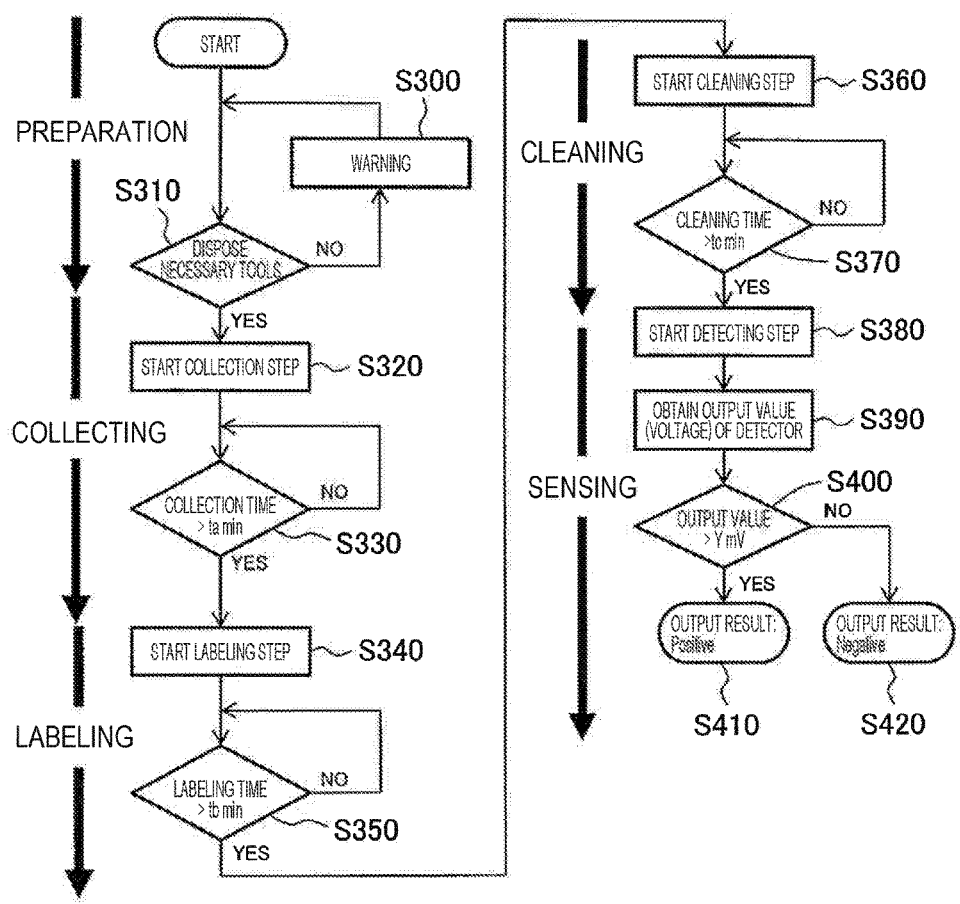
FIG. 13 is a flowchart of an examination step of the breath microorganism sensing device in Example 1 of the present invention.
Figure 14A:
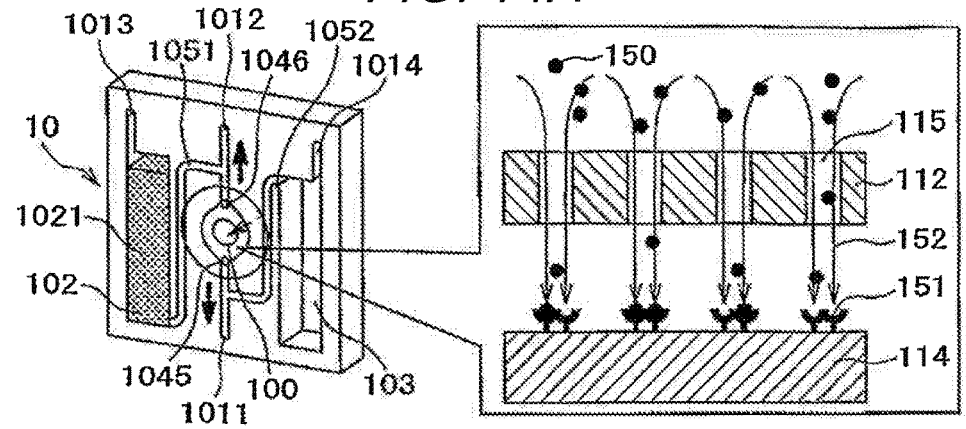
FIG. 14A is a diagram for describing a step of collecting a microorganism by a cartridge used in the breath microorganism sensing device in Example 1.
Figure 14B:
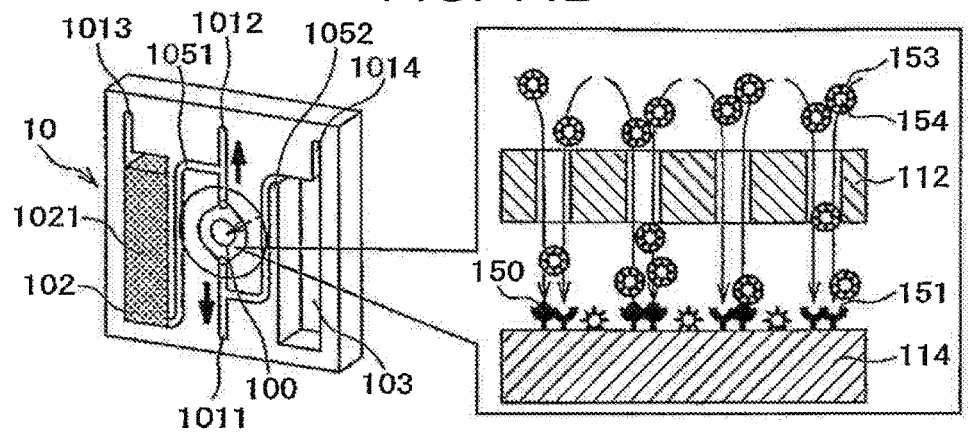
FIG. 14B is a diagram for describing a step of labeling a microorganism by the cartridge used in the breath microorganism sensing device in Example 1.
Figure 14C:
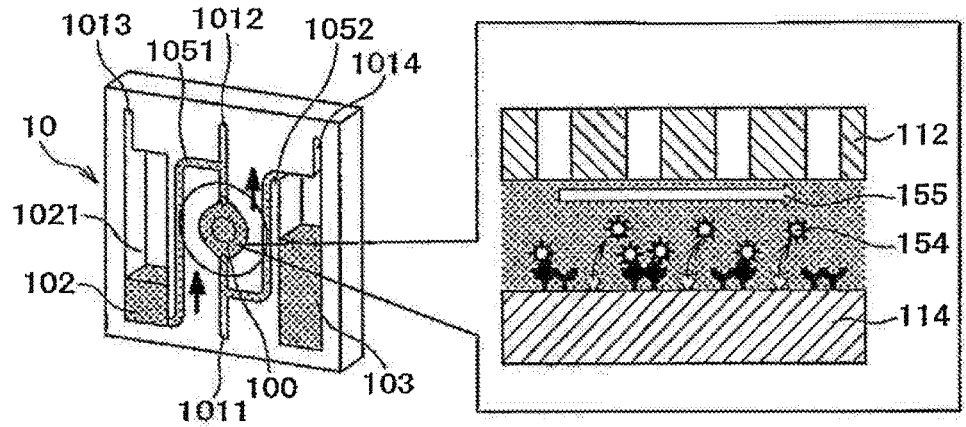
FIG. 14C is a diagram for describing a step of cleaning the cartridge used in the breath microorganism sensing device in Example 1.

After elapse of a set collecting time ta minutes, the step is shifted to a labeling step (FIG. 13). As illustrated in FIG. 14B, due to the open states (FIG. 12) of the valve 1312 of a pipe coupling the atomizer 123 to the inlet port 100 of the cartridge 10 and the valve 1313 coupling the vents 1011 and 1012 of the cartridge 10 to the pump 122, the mist 153 containing the fluorescence dye 154 and generated in the atomizer 123 is atomized in the cartridge 10 through the inlet port 100 of the cartridge 10 by a suctioning action of the pump 122. At this time, the mist 153 passes through the micropores 115 on the introduction plate 112, and collides with the collection plate 114. The mist 153 which has collided collides with the microorganism particle 150 collected on the surface of the collection plate 114, and the fluorescence dye 154 in the mist 153 is specifically bonded to the microorganism particle 150.

(4) Cleaning Step

After elapse of a set collecting time tb minutes, the step is shifted to a cleaning step (FIG. 13). As illustrated in FIG. 14C, due to the open states (FIG. 12) of the valve 1314 coupled to the vent 1013 of the cartridge 10 and the valve 1315 coupled to the vent 1014, the cleaning liquid 1021 in the cleaning liquid container 102 of the cartridge 10 flows into the waste container 103 through the cleaning liquid container-collecting and sensing part coupling flow path 1051, the collecting and sensing part 104, and the collecting and sensing part-waste container coupling flow path 1052 by a suctioning action of the pump 122.

At this time, the fluorescence dye 154 nonspecifically adsorbed by the collection plate 114 is removed together with water flow 155. The fluorescence dye 154 nonspecifically adsorbed by the collection plate 114 hinders sensing of microorganisms. Therefore, it is important to remove the fluorescence dye 154 as much as possible in order to perform sensing accurately.

(5) Sensing Step

After elapse of a set cleaning time tc minutes, the step is shifted to a sensing step (FIG. 13). The microorganism particle 150 is sensed by irradiating the collection plate 114 of the cartridge 10 with excitation light from the optical sensor 124 and sensing fluorescence of the fluorescence dye 154 bonded to the microorganism particle 150.

Figure 15:
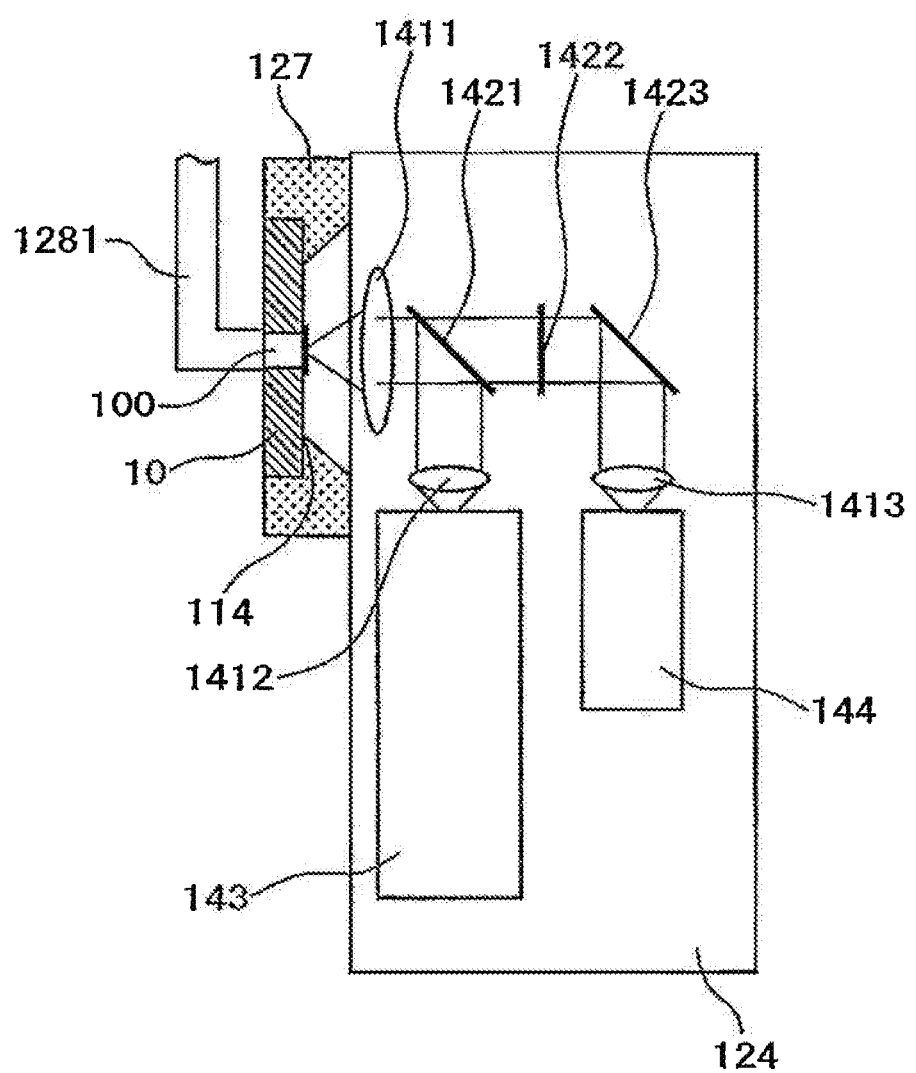
FIG. 15 is a diagram illustrating in detail an optical system of the breath microorganism sensing device in Example 1 of the present invention.
Figure 16:
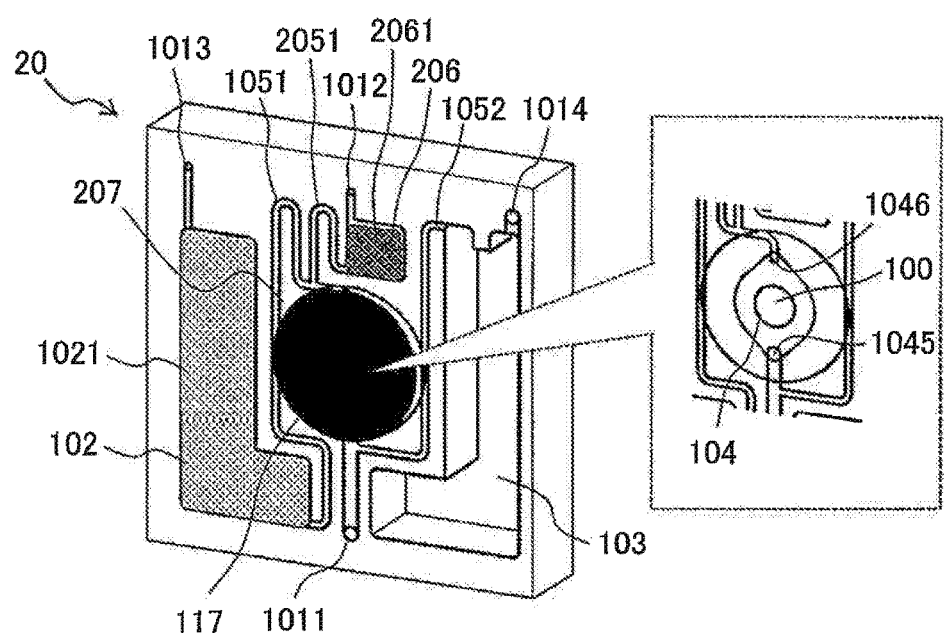
FIG. 16 illustrates a perspective view and a major enlarged view of a cartridge in Example 2 of the present invention.
Figure 17:
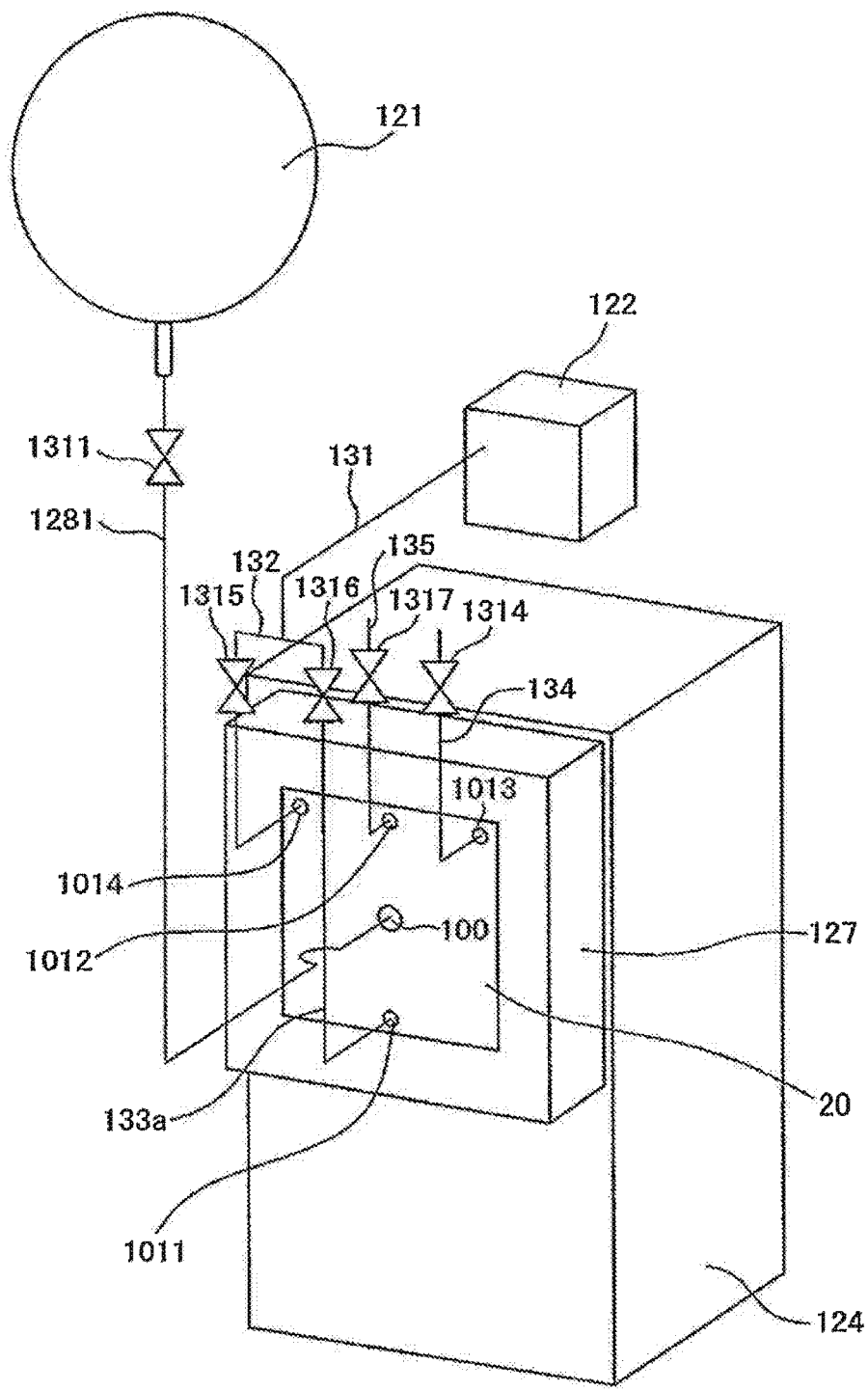
FIG. 17 is a diagram illustrating piping of a breath microorganism sensing device in Example 2 of the present invention using the cartridge illustrated in FIG. 16.
Figure 18A:
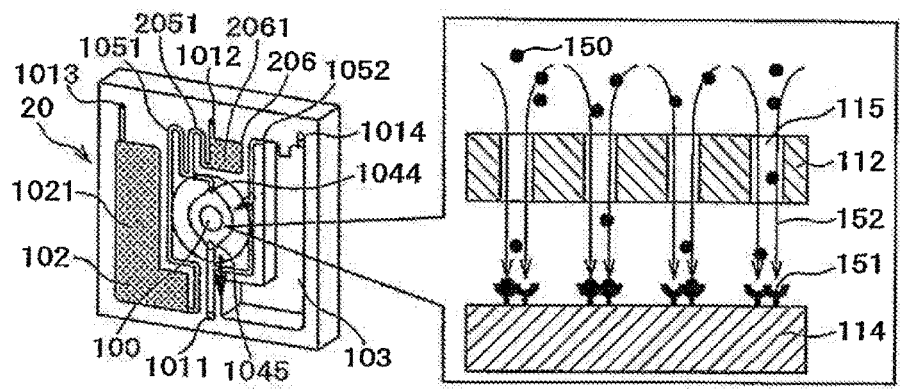
FIG. 18A is a diagram for describing a step of collecting a microorganism by the cartridge used in the breath microorganism sensing device in Example 2, illustrated in FIG. 17.
Figure 18B:
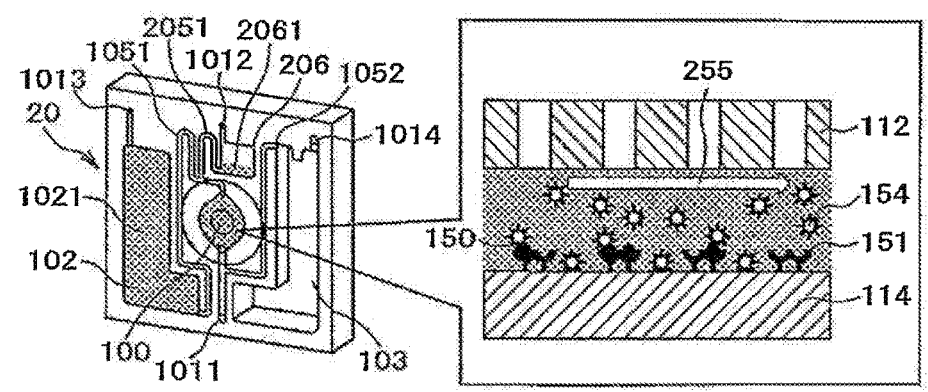
FIG. 18B is a diagram for describing a step of labeling a microorganism by the cartridge used in the breath microorganism sensing device in Example 2, illustrated in FIG. 17.
Figure 18C:
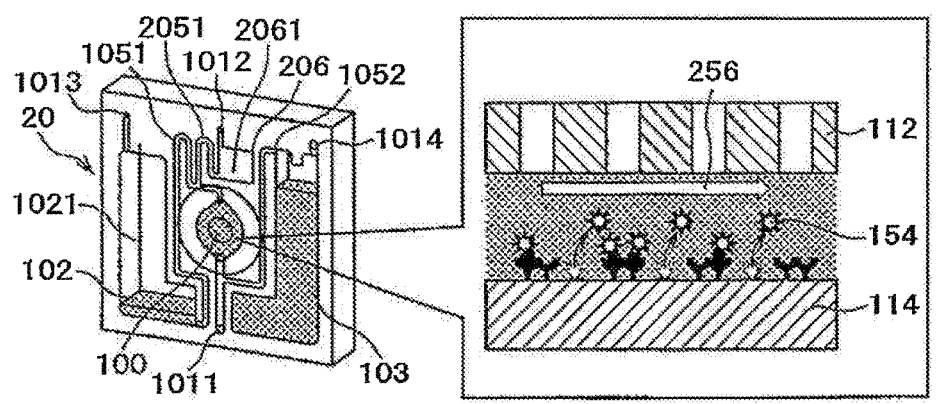
FIG. 18C is a diagram for describing a step of cleaning the cartridge used in the breath microorganism sensing device in Example 2, illustrated in FIG. 17.

FIG. 15 exemplifies an optical system of the optical sensor 124. The optical sensor 124 includes a light source 143 for emitting excitation light, an excitation light condensing lens 1412 for condensing excitation light emitted by the light source 143, a dichroic mirror 1421 for transmitting light in a wavelength region of fluorescence derived from a fluorescence dye bonded to the microorganism particle 150, an objective lens 1411 for condensing fluorescence derived from the fluorescence dye bonded to the microorganism particle 150 by irradiating the collection plate 114 with excitation light, a bandpass filter 1422 for transmitting only the light in the wavelength region of the fluorescence, a mirror 1423 for changing a light path of fluorescence, a fluorescence condensing lens 1413 for condensing fluorescence on a light sensor 144, and a light detector 144 for converting a light energy of fluorescence into an electric energy.

Any one of a laser, an LED, a mercury lamp, and a halogen lamp is preferably used for the light source 143. A photomultiplier tube or a semiconductor optical sensor is used for the light detector 144. In order to acquire the shape of the microorganism particle 150 collected on the collection plate 114, the light detector 144 may be replaced with an image acquisition device such as a CCD.

Light having a wavelength of 300 nm to 800 nm is used for excitation light. However, excitation light having a longer wavelength can suppress autofluorescence generated from the collection plate 114 or the introduction plate 112 more. Therefore, light having a wavelength of 600 nm or more is preferably used. The wavelength of fluorescence depends on the kind of fluorescence dye used, but is longer than that of excitation light.

In the sensing step, the light detector 144 acquires fluorescence derived from the microorganism particle 150 collected on the collection plate 114 as a voltage value (step S390). Then, the controller 125 compares the output value of the light detector 144 with a predetermined value Y (mV) (step S400). The value Y is a voltage value obtained by measuring fluorescence emitted from the collection plate 114 with the light detector 144 while a microorganism particle collected is not present. The value Y is measured at a certain point of time immediately before the step is shifted from the collecting step to the labeling step. When a detection value of the light detector 144 is larger than the predetermined value Y (mV), "Positive" is output to the display 126 or the like (step S410). When the detection value is not larger than the predetermined value Y (mV), "Negative" is output to the display 126 or the like.

EXAMPLE 2

In Example 1 above, in the labeling step, collected microorganism particles are bonded to a fluorescence dye by collision between a mist containing the fluorescence dye and the microorganism particles. However, microorganism particles can be bonded to the fluorescence dye by flow of a liquid containing the fluorescence dye on a surface of a collection plate on which the microorganism particles have been collected. Hereinafter, Example 2 in which the labeling step is performed by flow of a liquid containing a fluorescence dye on a surface of a collection plate will be described.

FIG. 16 is a perspective view of a cartridge 20 when viewed from the rear surface thereof, illustrating a structure of the cartridge 20 holding a liquid inside and including a structure for performing a step necessary for collecting and sensing microorganisms in breath or the air. The cartridge 20 includes an inlet port 100 into which breath or the air containing microorganisms flows, vents 1011 to 1014 for changing the atmosphere in the cartridge 20, a collecting and sensing part 104 for collecting and sensing microorganisms, a dye liquid container 206 for holding a fluorescence dye liquid 2061 specifically bonded to microorganisms, a cleaning liquid container 102 for holding a cleaning liquid 1021 for cleaning the collecting and sensing part 104, a waste container 103 for discarding the cleaning liquid 1021 which has passed through the collecting and sensing part 104, a dye liquid container-collecting and sensing part coupling flow path 2051 coupling the dye liquid container 206 to the collecting and sensing part 104 for making the dye liquid 2061 flow therein, a cleaning liquid container-collecting and sensing part coupling flow path 1052 coupling the cleaning liquid container 102 to the collecting and sensing part 104 for making the cleaning liquid 1021 flow therein, and a collecting and sensing part-waste container coupling flow path 1052 coupling the collecting and sensing part 104 to the waste container 103 for making the cleaning liquid 1021 flow therein. The enlarged view in FIG. 16 is a view for understanding the position of the inlet port 100 or the collecting and sensing part 104 in the cartridge 20, and does not illustrate a mask 117.

FIG. 17 is a diagram illustrating a positional relation between a pipe 131 for coupling a breath bag 121, the cartridge 20, and a pump 122 to one another, and valves 1311 and 1314 to 1317 for opening or closing the pipe 131 in the breath microorganism sensing device 1. The pipe 131 is coupled to vents 1011 and 1014 of the cartridge 20. The pipe 134 coupled to a vent 1013 has the valve 1314 interposed therein. An end of the pipe 134 is exposed to the atmosphere. A pipe 135 coupled to a vent 1012 has a valve 1317 interposed therein. An end of the pipe 135 is exposed to the atmosphere. As in Example 1, microorganism particles in breath are sensed according to the flowchart in FIG. 13. FIGS. 18A to 18C are diagrams for describing each step of collecting, labeling, and cleaning in the above flow for detecting microorganism particles in breath. These diagrams illustrate a flow state in the cartridge 20 and flow states of a microorganism particle 150 and a fluorescence dye 154 on a collection plate 114.

Hereinafter, each step will be described.

(1) Preparation Step

A preparation step is the same as in the cartridge 10 above; therefore, detailed description thereof will be omitted. A controller 125 checks whether the cartridge 20 or the breath bag 121 is mounted in step S310. When a necessary tool is not disposed or mounted, warning is displayed on a display 126 in step S300.

Table 2 indicates opening or closing of each of the valves 1311 and 1314 to 1317 in each step of collecting, labeling, cleaning, and sensing, and actions of the pump 122 and an optical sensor 124. FIGS. 18A to 18C illustrate a state of flow in the cartridge 20 in each step of collecting, labeling, and cleaning, and states of the microorganism particle 150 and the fluorescence dye 154 on the collection plate 114.

TABLE 2

| | Valve | | | | | Pump | Sensor |
|---|---|---|---|---|---|---|---|
| Step | 1311 | 1314 | 1315 | 1316 | 1317 | 122 | 124 |
| Collecting | Open | Close | Close | Open | Close | On | Off |
| Labeling | Close | Close | Open | Close | Open | On | Off |
| Cleaning | Close | Open | Open | Close | Close | On | Off |
| Sensing | Open | Open | Open | Open | Open | Off | On |

(2) Collecting Step

As illustrated in FIG. 18A, due to the open states (FIG. 17) of the valve 1311 of a pipe coupling the breath bag 121 to the inlet port 100 of the cartridge 20 and the valve 1316 coupling the vent 1011 of the cartridge 20 to the pump 122, breath in the breath bag 121 flows in the inlet port 100 of the cartridge 20 and the vent 1011 thereof by a suctioning action of the pump 122. Due to closed states of the valves 1317, 1314 and 1315 of a pipe coupled to the vents 1012, 1013, and 1014, the dye liquid 2061 in the dye liquid container 206 of the cartridge 20 and the cleaning liquid 2021 in the cleaning liquid container 202 thereof stay in the container.

At this time, the microorganism particles 150 contained in breath pass through the micropores 115 on the introduction plate 112, and collide with the collection plate 114. The microorganism particles 150 which have collided are specifically bonded to an antibody 151 bonded to the surface of the collection plate 114; therefore, the microorganism particles 150 are collected on the surface of the collection plate 114.

(3) Labeling Step

After elapse of a set collecting time ta minutes, the step is shifted to a labeling step (FIG. 13). As illustrated in FIG. 18B, due to the open states (FIG. 17) of the valve 1317 coupled to the vent 1012 of the cartridge 20 and the valve 1315 coupled to the vent 1014, the dye liquid 2061 in the dye liquid container 206 of the cartridge 20 flows into the waste container 103 through the dye liquid container-collecting and sensing part coupling flow path 2051, the collecting and sensing part 104, and the collecting and sensing part-waste container coupling flow path 1052 by a suctioning action of the pump 122. At this time, a liquid containing the fluorescence dye 154 flows on the collection plate 114 together with water flow 255, and the fluorescence dye 154 is specifically bonded to the microorganism particles 150 collected on the surface of the collection plate 114.

(4) Cleaning Step

After elapse of a set collecting time tb minutes, the step is shifted to a cleaning step (FIG. 13). As illustrated in FIG. 18C, due to the open states (FIG. 17) of the valve 1314 coupled to the vent 1013 of the cartridge 20 and the valve 1315 coupled to the vent 1014, the cleaning liquid 1021 in the cleaning liquid container 102 of the cartridge 20 flows into the waste container 103 through the cleaning liquid container-collecting and sensing part coupling flow path 1051, the collecting and sensing part 104, and the collecting and sensing part-waste container coupling flow path 1052 by a suctioning action of the pump 122.

At this time, the fluorescence dye 154 nonspecifically adsorbed by the collection plate 114 is removed together with water flow 256.

(5) Sensing Step

After elapse of a set cleaning time tc minutes, the step is shifted to a sensing step (FIG. 13). The microorganism particle 150 is sensed by irradiating the collection plate 114 of the cartridge 20 with excitation light from the optical sensor 124 and sensing fluorescence of the fluorescence dye 154 bonded to the microorganism particle 150.

EXAMPLE 3

In Examples 1 and 2 above, the amount of background light is reduced by using a physically opaque mask. However, by use of an image acquisition device such as a CCD camera for an optical sensor, an acquired image can be subjected to mask processing using an image processing technology. Hereinafter, Example of mask processing using an image processing technology will be described.

Figure 19:
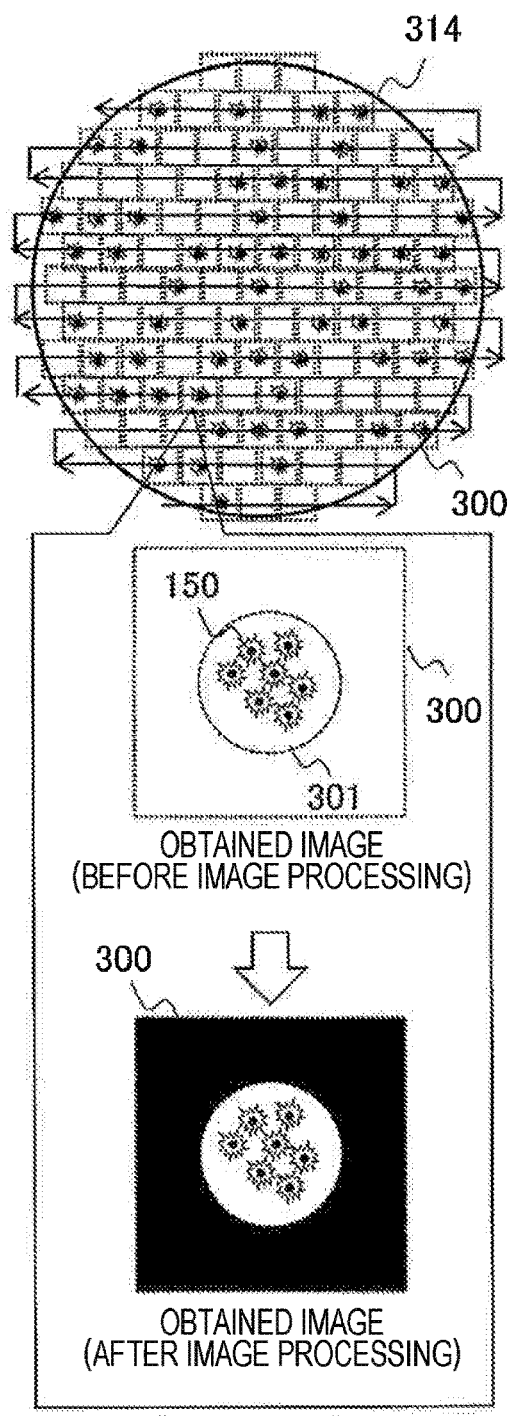
FIG. 19 is a diagram illustrating a sensing step of a breath microorganism sensing device in Example 3 of the present invention.

In the present Example, an image acquisition device such as a CCD camera is used for an optical sensor. Also in the present Example, as in Examples above, after steps of collecting, labeling, and cleaning are performed, the step is shifted to a sensing step. FIG. 19 is a diagram for describing procedures of the sensing step in the present Example. A part of a collection plate (imaging area 300) is imaged by an optical sensor in order to sense a microorganism particle 150 collected on a collection plate 314. When the area of the imaging area 300 is smaller than that of the collection plate 314, the imaging area 300 is changed by moving the optical sensor or a cartridge stepwise, and the entire collection plate 314 is imaged.

The number of the microorganism particle 150 can be evaluated by measurement of a total light amount on the collection plate 314 from the acquired image. As illustrated in FIG. 19, by converting a part other than a collision area 301 of microorganisms in the acquired image 300 into black (light amount=0) using an image processing technology, it is possible to largely reduce a light amount derived from an area in which the microorganism particle 150 has not collided and to improve an SN ratio (S represents a fluorescence amount derived from the microorganism particle 150, and N represents a fluorescence amount derived from a substance other than the microorganism particle 150). An example in which the light amount in an area other than the collision area of microorganisms is made to be "zero" has been shown. However, the S/N ratio can be improved by reducing the light amount in this area without necessarily making the light amount "zero".

As described above, according to Examples of the present invention, the introduction plate 112 and the collection plate 114 as impactors are disposed in a disposable cartridge; therefore, contamination on a side of the main body of the breath microorganism sensing device 1 can be reduced as much as possible. This makes erroneous detection less even after repeated use. A detection surface is formed on a side opposite to a collecting surface side used as an impactor of a cartridge, and the detection surface is made to be transparent. Therefore, optical detection can be performed from the rear side, and a breath microorganism sensing device can be downsized. An examiner only needs to attach a breath bag, and this is not a medical activity. Therefore, microorganisms can be detected automatically in a short time.

In Examples above, a porous plate is used as an introduction plate. However, when a detection object is relatively large, the detection object may be detected with one micropore. In this case, the detection object can be specified more accurately.

REFERENCE SIGNS LIST 1 breath microorganism sensing device (airborne substance sensing device)
10, 20 cartridge
100 inlet port
102 cleaning liquid container
103 waste container
104 collecting and sensing part
106 reagent container
110 main body
112 introduction plate
114 collection plate
115 micropore
116 vent
117 opaque mask
118 opening window
121 breath bag
122 pump
123 atomizer
124 optical sensor
150 microorganism particle (airborne substance)

The invention claimed is:

1. A cartridge for an airborne substance sensing device, comprising:
   an introduction plate on which at least one micropore through which a gas containing an airborne substance can pass is formed;
   a transparent collection plate disposed so as to face the introduction plate and capable of collecting the airborne substance due to collision of the airborne substance caused by collision of the gas which has passed through the micropore;
   a main body in which the introduction plate and the collection plate are disposed in parallel and a flow path for guiding the gas containing the airborne substance to the micropore is formed; and
   an opaque mask covering the collection plate and provided with at least one opening window through which light can pass at a position corresponding to a collection area on the collection plate in which the airborne substance is collected by collision; wherein
   the opening window of the mask is disposed so as to overlap with the area in which the airborne substance is captured and so as to have an area the same as or larger than the area in which the airborne substance is captured;
   the number of the at least one opening window of the mask is equal to that of the at least one micropore;
   the cartridge is formed such that a gas containing an airborne substance flows along a surface of the collection plate from the center to the outer periphery;
   the opening window of the mask is formed so as to deviate to the outer periphery of the collection plate with respect to a position of the corresponding micropore with a predetermined amount; and the deviation amount of the opening window of the mask is not larger than the diameter of the micropore.

2. The cartridge for an airborne substance sensing device according to claim 1, wherein
the opening window of the mask has a larger amount of the deviation on a side of the outer periphery than at the center of the collection plate.

3. The cartridge for an airborne substance sensing device according to claim 2, wherein
the opening window of the mask is formed so as to have a gradually larger deviation amount from the center of the collection plate toward the outer periphery.

4. The cartridge for an airborne substance sensing device according to claim 1, wherein
the opaque mask covers a surface of the collection plate opposite to the collection area, and
the airborne substance collected on the collection area is sensed.

5. The cartridge for an airborne substance sensing device according to claim 1, comprising:
a single or a plurality of containers for holding a liquid;
a flow path for coupling a space between the introduction plate and the collection plate to the containers;
a waste container for storing the liquid which has flown between the introduction plate and the collection plate; and
a flow path for coupling the space between the introduction plate and the collection plate to the waste container.

6. The cartridge for an airborne substance sensing device according to claim 1, wherein
an adhesive substance or a substance to be specifically bonded to the airborne substance is bonded or adsorbed to the surface of the collection plate on which the airborne substance is captured.

7. The cartridge for an airborne substance sensing device according to claim 1, wherein
the airborne substance is formed of any microparticles of viruses, bacteria, yeast, protozoa, fungi, spores, pollen, animal skin debris, mite excrement and carcasses, house dust, exhaust gas particles, and ore particles.

8. The cartridge for an airborne substance sensing device according to claim 1, wherein
the introduction plate is transparent.

9. An airborne substance sensing device using the cartridge according to claim 1, comprising:
a pump for generating a flow of air in a direction from the introduction plate to the collection plate; and
an optical sensor for optically sensing the airborne substance captured on the collection plate, wherein
the optical sensor is disposed on the rear side of a collection surface of the collection plate.

10. The airborne substance sensing device according to claim 9, wherein
a breath bag in which breath of a patient is enclosed is coupled to the airborne substance sensing device, and the airborne substance in the breath bag is thereby collected on the collection plate of the cartridge and is sensed.

11. The airborne substance sensing device according to claim 9, wherein an air bag in which the air in an environment is enclosed is coupled to the airborne substance sensing device, and the airborne substance in the air bag is thereby collected on the collection plate of the cartridge and is sensed.

12. A cartridge for an airborne substance sensing device, comprising:

an introduction plate on which at least one micropore through which a gas containing an airborne substance can pass is formed;
a transparent collection plate disposed so as to face the introduction plate and capable of collecting the airborne substance due to collision of the airborne substance caused by collision of the gas which has passed through the micropore;
a main body in which the introduction plate and the collection plate are disposed in parallel and a flow path for guiding the gas containing the airborne substance to the micropore is formed; and
an opaque mask covering the collection plate and provided with at least one opening window through which light can pass at a position corresponding to a collection area on the collection plate in which the airborne substance is collected by collision; wherein
the opening window of the mask is disposed so as to overlap with the area in which the airborne substance is captured and so as to have an area the same as or larger than the area in which the airborne substance is captured;
the number of the at least one opening window of the mask is equal to that of the at least one micropore;
the cartridge is formed such that a gas containing an airborne substance flows along a surface of the collection plate from the center to the outer periphery;
the opening window of the mask is formed so as to deviate to the outer periphery of the collection plate with respect to a position of the corresponding micropore with a predetermined amount; and
the area of the opening window of the mask is smaller than four times the area of the micropore.

13. An airborne substance sensing device using a cartridge according to claim 12, comprising:
a pump for generating a flow of the air in a direction from the introduction plate to the collection plate; and
an image acquisition device for optically sensing the airborne substance captured on the collection plate, wherein
the image acquisition device is disposed on the rear side of the collection plate, and reduces a light amount in an area other than a collision area of the airborne substance collected on the collection surface using image processing.

14. An airborne substance sensing device using a cartridge for an airborne substance sensing device, comprising:
an introduction plate on which at least one micropore through which a gas containing an airborne substance can pass is formed;
a transparent collection plate disposed so as to face the introduction plate and capable of collecting the airborne substance due to collision of the airborne substance caused by collision of the gas which has passed through the micropore;
a main body in which the introduction plate and the collection plate are disposed in parallel and a flow path for guiding the gas containing the airborne substance to the micropore is formed;
an opaque mask covering the collection plate and provided with at least one opening window through which light can pass at a position corresponding to a collection area on the collection plate in which the airborne substance is collected by collision;
a single or a plurality of containers for holding a liquid;
a flow path for coupling a space between the introduction plate and the collection plate to the containers;

a waste container for storing the liquid which has flown between the introduction plate and the collection plate;

a flow path for coupling the space between the introduction plate and the collection plate to the waste container;

a pump for generating a flow of the air in a direction from the introduction plate to the collection plate; and an optical sensor for optically sensing the airborne substance captured on the collection plate; wherein the airborne substance sensing device makes the liquid in the container flow to the waste container though a space between the introduction plate and the collection plate with the pump.

15. The airborne substance sensing device according to claim 14, wherein the opening window of the mask is disposed so as to overlap with the collection area in which the airborne substance is collected and so as to have an area the same as or larger than the collection area in which the airborne substance is collected.

16. The airborne substance sensing device according to claim 14, wherein the number of the at least one opening window of the mask is equal to that of the at least one micropore.

17. The airborne substance sensing device according to claim 14, wherein the liquid contains a fluorescence dye to be specifically bonded to the airborne substance.

18. The airborne substance sensing device according to claim 14, wherein the liquid is a liquid containing a fluorescence dye to be specifically bonded to the airborne substance or a liquid for cleaning off the fluorescence dye attached to the collection plate from the collection plate.

* * * * *